United States Patent [19]

Banner et al.

[11] Patent Number: 5,451,600
[45] Date of Patent: Sep. 19, 1995

[54] SUBSTITUTED TETRAHYDROBENZOPYRROLYL-FURANOIC ACID DERIVATIVES AS PHOSPHOLIPASE $A_2$ INHIBITORS

[75] Inventors: Bruce L. Banner, Wayne; Giuseppe F. Weber, Cedar Grove, both of N.J.

[73] Assignee: Hoffmann-La Roche Inc., Nutley, N.J.

[21] Appl. No.: 230,035

[22] Filed: Apr. 19, 1994

[51] Int. Cl.[6] ............ A61K 31/40; C07D 407/06; C07D 407/12; C07D 407/02
[52] U.S. Cl. .................... 514/414; 548/448; 548/449
[58] Field of Search ............... 548/449, 448; 514/414

[56] References Cited

FOREIGN PATENT DOCUMENTS 04254060  9/1992  Japan .

Primary Examiner—Robert Gerstl
Attorney, Agent, or Firm—George M. Gould; George W. Johnston; Robert A. Silverman

[57] ABSTRACT

Compounds of the formula

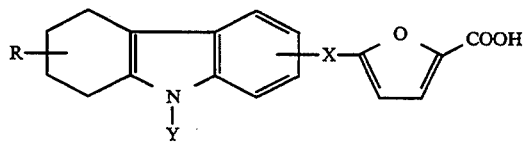

wherein R is hydrogen, alkyl$_{1-8}$, geminal alkyl$_{1-3}$, unsubstituted or substituted aryl; X is alkylene, —CR$_1$=CR$_2$— (E and/or Z), carbonyl, oxygen or sulfur, wherein one of R$_1$ and R$_2$ is alkyl$_{1-3}$ and the other is hydrogen; Y is unsubstituted alkyl$_{1-12}$ or substituted by one or more alkyl$_{1-3}$ groups, or unsubstituted or substituted phenylalkyl $_{1-3}$; or a salt thereof with a pharmaceutically acceptable base, are described.

The compound of formula I are potent inhibitors of phospholipase $A_2$ (PLA$_2$) and are therefore useful in the treatment of inflammatory diseases, such as, psoriasis, inflammatory bowel disease, asthma, allergy, arthritis, dermatitis, gout, pulmonary, myocardial ischemia and trauma induced inflammation, such as, spinal cord injury.

29 Claims, No Drawings

SUBSTITUTED TETRAHYDROBENZOPYRROLYLFURANOIC ACID DERIVATIVES AS PHOSPHOLIPASE A₂ INHIBITORS

BRIEF DESCRIPTION OF THE INVENTION

The invention relates to compounds of the formula

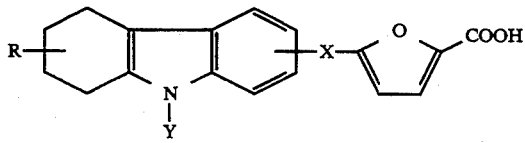

wherein R is hydrogen, alkyl$_{1-8}$, geminal alkyl$_{1-3}$, unsubstituted or substituted aryl; X is alkylene, —CR$_1$=CR$_2$— (E and/or Z), carbonyl, oxygen or sulfur, wherein one of R$_1$ and R$_2$ is alkyl$_{1-3}$ and the other is hydrogen; Y is unsubstituted alkyl$_{1-12}$ or substituted by one or more alkyl$_{1-3}$ groups, or unsubstituted or substituted phenylalkyl $_{1-3}$; and salts thereof with pharmaceutically acceptable bases.

The compound of formula I are potent inhibitors of phospholipase A$_2$ (PLA$_2$) and are therefore useful in the treatment of inflammatory diseases, such as, psoriasis, inflammatory bowel disease, asthma, allergy, arthritis, dermatitis, gout, pulmonary, myocardial ischemia and trauma induced inflammation, such as, spinal cord injury.

In another aspect, the invention relates to methods compositions and intermediates, that is the compounds of formula IV to VI.

DETAILED DESCRIPTION OF THE INVENTION

The invention relates to compounds of the formula

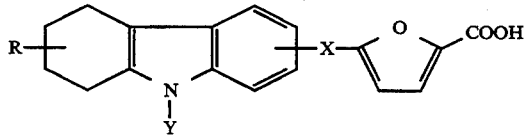

wherein R is hydrogen, alkyl$_{1-8}$, geminal alkyl$_{1-3}$, unsubstituted or substituted aryl; X is alkylene, —CR$_1$=CR$_2$— (E and/or Z), carbonyl, oxygen or sulfur, wherein one of R$_1$ and R$_2$ is alkyl$_{1-3}$ and the other is hydrogen; Y is unsubstituted alkyl$_{1-12}$ or substituted by one or more alkyl$_{1-3}$ groups, or unsubstituted or substituted phenylalkyl $_{1-3}$; and salts thereof with pharmaceutically acceptable bases.

The compound of formula I are potent inhibitors of phospholipase A$_2$ (PLA$_2$) and are therefore useful in the treatment of inflammatory diseases, such as, psoriasis, inflammatory bowel disease, asthma, allergy, arthritis, dermatitis, gout, pulmonary, myocardial ischemia and trauma induced inflammation, such as, spinal cord injury.

As used herein, the term "alkyl" denotes, alone or in combination, straight or branched chain, saturated hydrocarbon residues of 1–7 carbon atoms, unless otherwise stated, for example, methyl, ethyl, n-propyl, isopropyl, n-butyl, isobutyl, sec.-butyl, t-butyl, pentyl, hexyl, and the like.

The term "alkoxy" denotes an alkyl ether group in which the alkyl group is straight or branched chain hydrocarbon residue is of 1 to 7 carbon atoms, for example, methoxy, ethoxy, propoxy, isopropoxy, butoxy, isobutoxy, sec.-butoxy, t-butoxy and the like.

The term "phenylalkyl$_{1-3}$" denotes residue with 7–9 carbon atoms which is optionally mono- or multiply-substituted by alkyl, alkoxy, hydroxy, halogen, trifluoromethyl or nitro.

The term "aryl" denotes a mono- or bicyclic aromatic hydrocarbon residue with 6–14 carbon atoms which is optionally mono- or multiply-substituted by alkyl, alkoxy, hydroxy, halogen, trifluoromethyl or nitro, for example, phenyl, α- or β-naphthyl, indenyl, anthryl or phenanthryl and the like.

The term "alkylene" denotes to a straight chain divalent substituent consisting solely by carbon and hydrogen of from 1 to 7 carbon atoms which may be substituted by one or more alkyl groups. Examples of alkylene groups are methylene, ethylene, propylene and the like.

A preferred group of compounds comprise those of formula I wherein X is O or alkylene, Y is alkyl 4-9, phenylalkyl$_{1-3}$, and R is hydrogen, geminal dimethyl, n-octyl or phenyl.

A more preferred group of compounds comprise those of formula I wherein X is O, carbonyl or alkylene, R is hydrogen or geminal dialkyl$_{1-3}$ and Y is n-octyl.

A still more preferred group of compounds comprise those of formula I wherein X is O, —CH=CH—(Z) or straight chain alkylene, R is hydrogen, and Y is n-octyl. Preferred compounds of formula I of the invention are:

- 5- [[1,2,3,4-tetrahydro-9-(4-chlorophenyl)methyl-9H-dibenzo[b,d]pyrrol-6-yl]oxy]-2-furancarboxylic acid;
- (E)-5-[2-(1,2,3,4,-Tetrahydro-1,1 -dimethyl-9-octyl-9H-dibenzo[b,d]pyrrol-6-yl)-ethenyl]-2-furancarboxylic acid;
- (E)-5-[2-Methyl-2-(1,2,3,4-tetrahydro- 1,1 -dimethyl-9- octyl-9H -dibenzo[b,d]-pyrrol-6-yl)ethenyl]-2-furancarboxylic acid;
- (Z)-5-[2-(1,2,3,4-Tetrahydro-9-octyl-9H-dibenzo[b,d]pyrrol-6-yl)ethenyl]-2-furancarboxylic acid;
- 5-[2-(1,2,3,4-Tetrahydro-9-octyl-9H-dibenzo[b,d]pyrrol-6-yl) ethyl]-2-furancarboxylic acid;
- 5-[(1,2,3,4-Tetrahydro-9-octyl-9H-dibenzo[b,d]pyrrol-6-yl) oxy]-2-furancarboxylic acid;
- 5-[(1,2,3,4-Tetrahydro-9-octyl-9H-dibenzo[b,d]pyrrol-7-yl) oxy]-2-furancarboxylic acid;
- 5-[(1,2,3,4-Tetrahydro-9-octyl-9H-dibenzo[b,d]pyrrol-6-yl) carbonyl]-2-furancarboxylic acid; and
- 5-[(1,2,3,4-Tetrahydro-9-octyl-9H-dibenzo[b,d]pyrrol-6-yl) methyl]-2-furancarboxylic acid. Other exemplary compounds of the invention are:
- rac-(Z)-5-[2-(1,2,3,4-Tetrahydro- 1,9-dioctyl-9H-dibenzo[b,d]pyrrol-6-yl)ethenyl]-2-furancarboxylic acid;
- rac-(Z)-5-[2-(1,2,3,4-Tetrahydro- 1-octyl- 9-(4-chlorophenyl) methyl-9 H-dibenzo[b,d]pyrrol-6-yl) ethenyl-2-furancarboxylic acid;
- (Z)-5-[2-(1,2,3,4-Tetrahydro- 1,1 -dimethyl-9-(4-chlorophenyl) methyl-9H-dibenzo[b,d]pyrrol-6-yl) ethenyl]-2-furancarboxylic acid;
- rac-5-[(1,2,3,4-Tetrahydro- 1-butyl-9-octyl-9H-dibenzo [b,d]pyrrol-6-yl)oxy]-2-furancarboxylic acid;

rac-5-[(1,2,3,4-Tetrahydro- 1-butyl-9-(4-chlorophenyl) methyl-9H-dibenzo[b,d]pyrrol-6-yl)oxy]-2-furancarboxylic acid; and the like.

The compounds of formula I can be prepared, as hereinafter described in Reaction Schemes I–VI.

SCHEME I

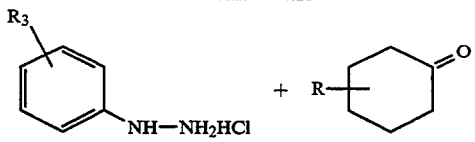

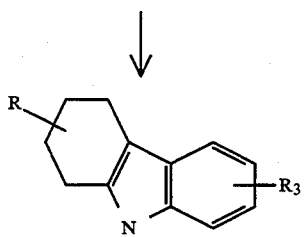

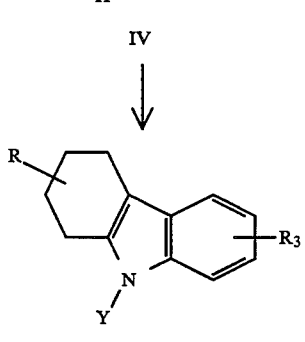

wherein R and Y are as previously described and $R_3$ is alkoxycarbonyl, cyano or —X—CH$_2$—Ph.

In Reaction Scheme I, a compound of formula II, which are known compounds or can be prepared according to known methods, undergoes a Fisher-Indole condensation reaction with a compound of formula III, which are known compounds or can be prepared according to known methods, utilizing known reaction condition, to yield the corresponding compound of formula IV, which can be separated or recovered from the reaction mixture utilizing known procedures, such as, chromatography, crystallization or the like.

The resulting compound of formula IV is alkylated to the corresponding compound of formula V utilizing a known alkylating agent, for example, a haloalkane, such as, 1-bromooctane, or the like, with a base, for example, potassium carbonate, potassium hydroxide or the like, and in the presence of a catalyst, such as, tetrabutylammonium bromide to yield the corresponding compound of formula V. The reaction is carried under anhydrous conditions, in a inert solvent, preferably toluene, at the reflux temperature of the reaction mixture. The resulting compound of formula V can be separated or recovered from the reaction mixture utilizing known procedures, for example, chromatography, crystallization or the like.

SCHEME II

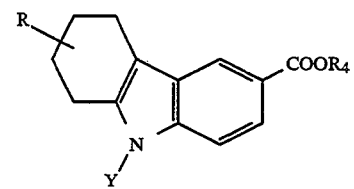

wherein R and Y are as previously described, $R_4$ is lower alkyl and $R_1'$ is hydrogen.

In Reaction Scheme II, a compound of formula Va is reduced to yield the corresponding alcohol of formula VI with a reducing agent, such as, lithium aluminum hydride, DIBAH or the like, in the presence of a solvent, such as, ether, THF, methylene chloride or the like.

The resulting compound of formula VI is treated with triphenylphosphine hydrobromide to yield the corresponding phosphonium salt of formula VIIa, using a methylene chloride, toluene or acetonitrile, as a solvent. The resulting compound of formula VIIa can be recovered by crystallization or the like.

SCHEME III

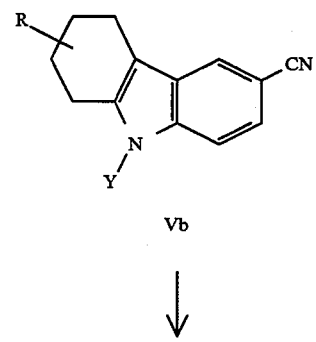

-continued
SCHEME III

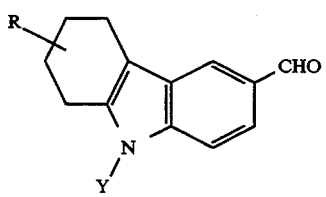

VIII

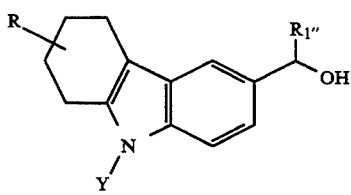

IX

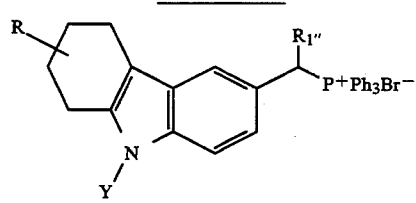

VIIb wherein R and Y are as previously described and $R_1''$ is lower alkyl.

In Reaction Scheme III, a compound of formula Vb is reduced to an aldehyde by using, for example, DIBAH in toluene to yield the corresponding compound of formula VIII by chromatographic purification and crystallization.

The resulting compound of formula VIII is treated with a Grignard reagent, such as, methylmagnesium bromide or the like, to yield the corresponding compound of formula IX, which can be recovered utilizing standard methods such as, crystallization.

The resulting compound of formula IX is treated with triphenyl-phosphine hydromide in a solvent, such as, toluene, methylene-chloride or acetonitrile, to yield the corresponding compound of formula VIIb which can be recovered utilizing standard methods, such as, crystallization or the like.

SCHEME IV

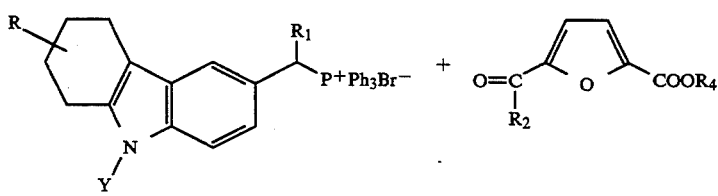

VII                                X

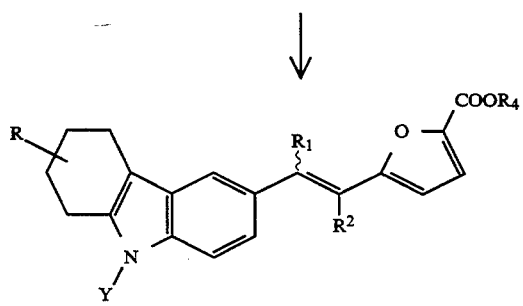

XI

-continued
SCHEME IV

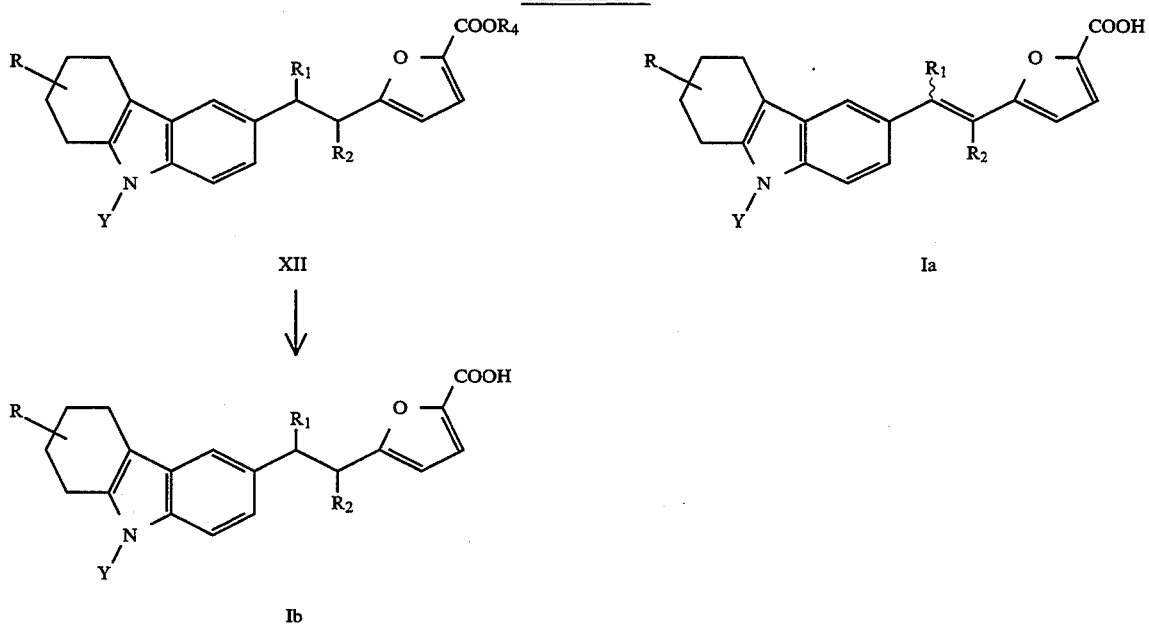

wherein R, $R_1$, $R_2$, $R_4$ and Y are as previously described, provided that when $R_1$ is hydrogen, $R_2$ is alkyl, and when $R_1$ is alkyl, $R_2$ is hydrogen.

In Reaction Scheme IV, a compound of formula VII undergoes a Wittig condensation reaction with a compound of formula X, in the presence of a base such as, sodium methoxide, sodium hydride or the like, to yield the corresponding compound of formula XI which was recovered according to standard procedures.

The resulting compound of formula XI is hydrolized to the corresponding acid of formula Ia by using lithium hydroxide, sodium hydroxide or the like, in a polar solvent, such as, methanol, tetrahydrofuran and water, or the like. The resulting compound of formula Ia can be purified by conventional methods, such as, crystallization or chromatography.

Alternatively, a compound of formula X is hydrogenated at normal pressure and room temperature in the presence of 10% Palladium on carbon in a solvent, such as, ethyl acetate, ethanol or the like, to yield the corresponding compound of formula XII, which can be recovered utilizing standard procedures.

The resulting compound formula XII is hydrolized to the corresponding acid of formula Ib utilizing a base, such as, lithium hydroxide, sodium hydroxide or the like, with a solvent, such as, methanol, isopropyl alcohol or a mixture of tetrahydrofuran and water. The resulting compound of formula Ib can be recovered utilizing standard procedures.

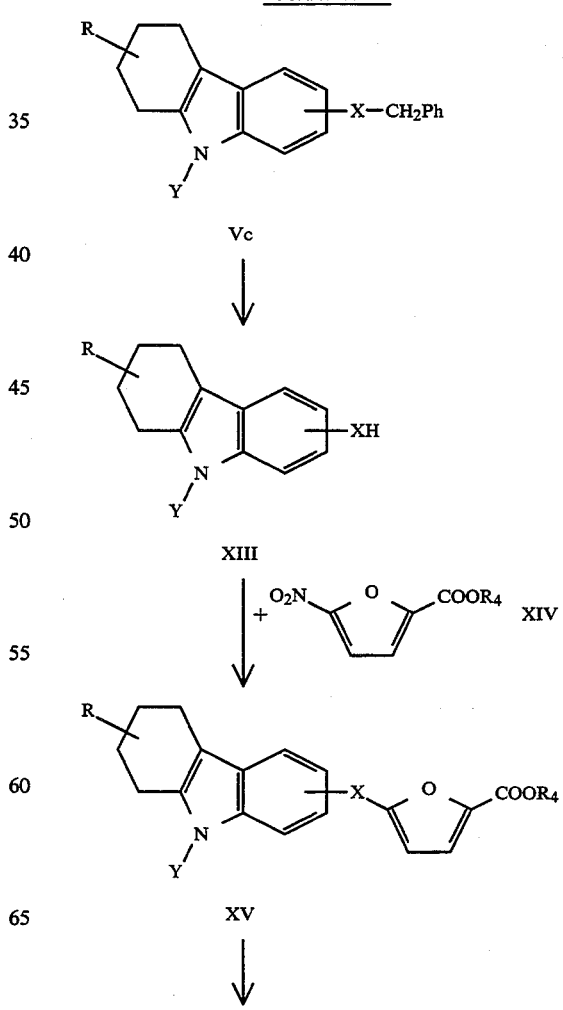

-continued
SCHEME V

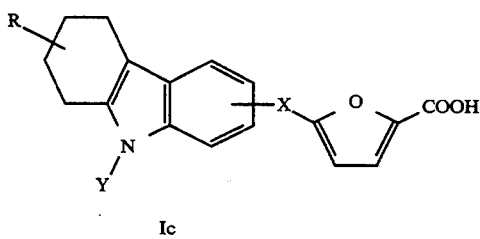

Ic wherein X is O or S and R, $R_4$, and Y are as previously described.

In Reaction Scheme V, a compound of formula Vc is hydrogenated at normal pressure and at room temperature using a catalyst, such as, 10% palladium on carbon with a solvent, such as, ethanol, ethyl acetate or acetic acid, to yield the corresponding compound of formula XIII, which can be recovered utilizing standard procedures.

The resulting compound of formula XIII is reacted with a compound of formula XIV in the presence of a base, such as, sodium hydride or the like, in dimethylsulfoxide to yield the corresponding compound of formula XV, which can be recovered by utilizing standard procedures.

The resulting compound of formula XV is hydrolized to the corresponding acid of formula Ic with a base, such as, lithium hydroxide, sodium hydroxide or the like, in a polar solvent, such as, methanol, ethanol or a mixture of tetrahydrofuran and water. The resulting compound of formula Ic can be recovered utilizing standard procedures.

SCHEME VI

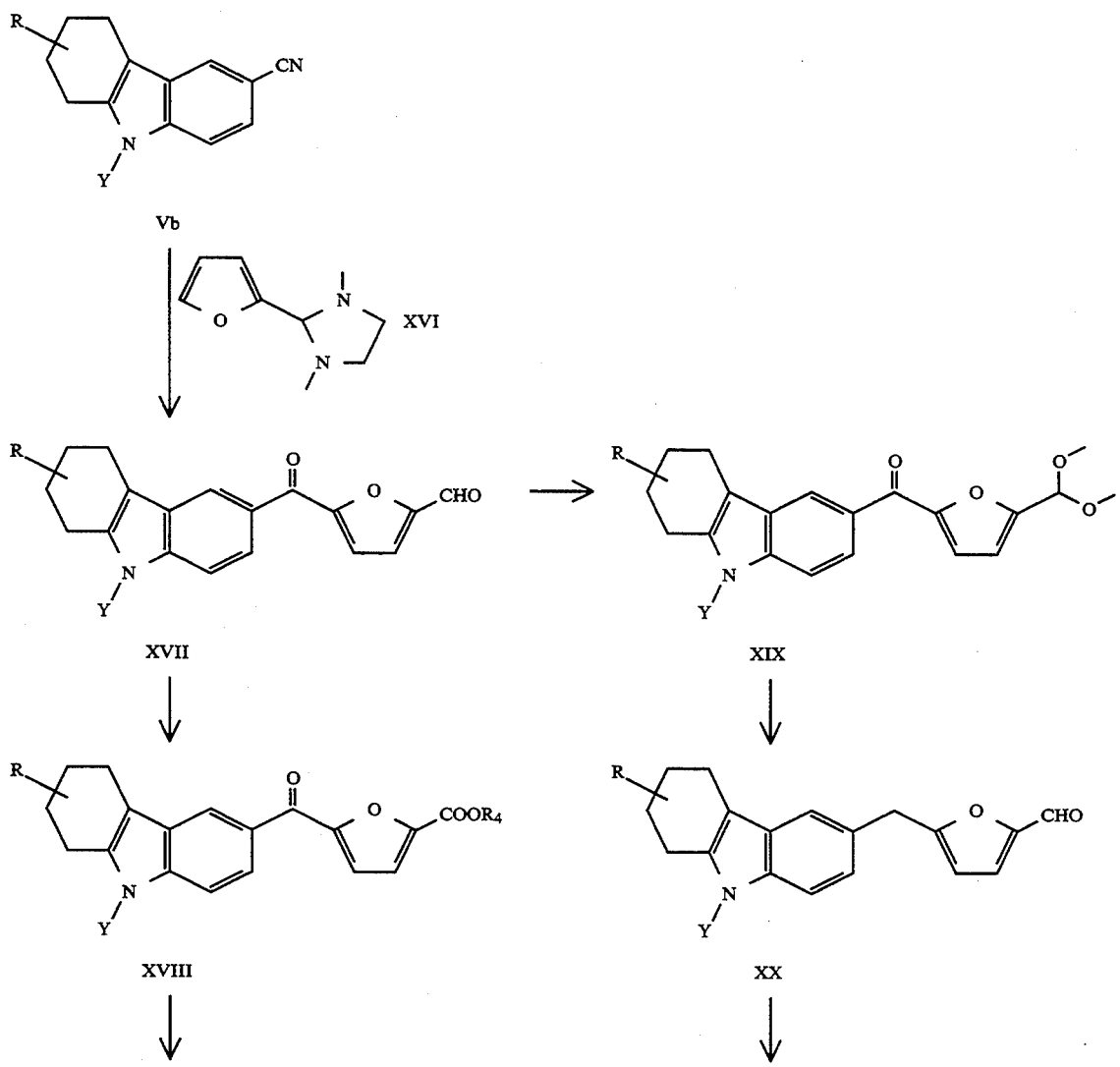

-continued
SCHEME VI

Id

Ie wherein R, $R_4$ and Y are as previously described.

In Reaction Scheme VI, a compound of formula Vb is treated with a compound of formula XVI in the presence of a base, such as, n-butyllithium in a solvent, such as, tetrahydrofuran and quenched in aqueous mineral acid to yield the corresponding compound of formula XVII which can be recovered utilizing standard procedures.

The resulting compound of formula XVII is oxidized to the corresponding ester of formula XVIII utilizing an oxidizing agent, such as, activated manganese dioxide in the presence of sodium cyanide and acetic acid and in a polar solvent, such as, methanol. The compound of formula VIII can be recovered by conventional methods, such as, chromatography or crystallization.

A compound of formula XVIII is hyrolized to the corresponding acid of formula Id with a base such as, sodium hydroxide, lithium hydroxide and a solvent, such as, methanol ethanol or a mixture of tetrahydrofuran and water. The acid was recovered utilizing standard procedures. A compound of formula XVII is refluxed in methanol in the presence of a Lewis acid, such as, p-toluenesulfonic acid, or mineral acid to yield the corresponding compound of formula XIX which can be recovered by using standard procedures.

A compound of formula XIX is reduced with hydrazine in the presence of potassium carbonate in triethyleneglycol as a solvent, followed by treatment in aqueous mineral acid to yield a compound of formula XX.

The compound is then recovered by utilizing standard procedures. Compound of formula XX is oxidized to the corresponding acid of formula Ie by an oxidating agent, such as, silverdioxide in a solvent such as, ethanol. The compound is recovered by crystallization.

In the Reaction Schemes, a compound of formula II, Lists of compounds of formula II:
6-carbethoxyphenylhydrazine hydrochloride;
4-hydrazinobenzonitrile monohydrochloride; and the like.
which are known compounds or can be prepared according to known methods, is reacted with a compound of formula III,
Lists of compounds of formula III:
cyclohexanone;
1,1-dimethylcyclohexanone;
4,4-dimethylcyclohexanone;
3,3,5,5-tetramethylcyclohexanone;
cyclopentanone;
cycloheptanone;
cyclooctanone;
cyclodecanone;
cyclododecanone;
2-(3-methoxyphenyl)cyclohexanone);
2-octylcyclohexanone; and the like.

which are known compounds or can be prepared to yield the corresponding compound of formula IV, which can be separated or recovered from the reaction mixture utilizing known procedures such as chromatography, crystallization or the like.

The invention also relates to salts of the compounds of formula I which lend themselves to salt formation with a base. Salts of the compounds of formula are prepared by the reaction with a base having a non-toxic, pharmacologically acceptable cation. In general, any base which will form a salt with a carboxylic acid and whose pharmacological properties will not cause an adverse physiological effect is within the scope of this invention.

Suitable bases thus include, for example, the alkali metal and alkaline earth metal hydroxides, carbonates or the like, for example, calcium hydroxide, sodium hydroxide, sodium carbonate, potassium carbonate or the like, ammonia, primary, secondary and tertiary amines, such as monoalkylamines, dialkylamines, trialkylamines, for example, methylamine, diethylamine, triethylamine or the like, nitrogen containing heterocyclic amines, for example, piperidine or the like. A salt thus produced is the functional equivalent of the corresponding acids of formula I and one skilled in the art will appreciate that the variety of salts embraced by the invention is limited only by the criterion that a base employed in forming the corresponding salts be both non-toxic and physiologically and pharmaceutically acceptable.

The compounds of formula I are potent inhibitors of phospholipases $A_2$ ($PLA_2$'s) and are therefore useful in the treatment of diseases, such as, psoriasis, inflammatory bowel disease, asthma, allergy, arthritis, dermatitis, gout, pulmonary disease, myocardial ischemia, and trauma induced inflammation, such as, spinal cord injury.

The useful activity of the compounds of formula I as phospholipase $A_2$ ($PLA_2$) inhibitors can be demonstrated as hereinafter set forth below.

Methods for Evaluating Phospholipase $A_2$ Inhibitors

1, Phospholipase $A_2$ ($PLA_2$) enzymatic assay - % Inhibition of HSF-$PLA_2$ $PLA_2$ assay procedure described by Hope et al., Inflammation 14:543–559 (1.990) was utilized to measure the inhibitory activity of the invention (inhibitor) against $PLA_2$ activity in human synovial fluid (HSF). Synovial fluid was obtained from patients with rheumatoid arthritis. The assay procedure measured the release of [1-$^{14}$C]oleic acid from the sn-2 position of phospholipids in autoclaved *Escherichia coli* previously grown in media containing [1-$^{14}$C]oleic acid. The standard assay reaction conditions included $1 \times 10^9$ *Escherichia coil* (10,000 dpm $^{14}$C), 0.15% (v/v) cell-depleted HSF, (which was equivalent to 66 μg protein/mL) 2 mM CaCl$_2$, 150 mM NaCl, 50 mM sodium (N-[2-hydroxyethyl] piperazine-N'-[2-ethanesulfonate]) (HEPES) buffer (pH 7.3), 1% dimethyl sulfoxide (DMSO) and various concentrations of inhibitor in a total volume of 0.5 ml. Inhibitors were dissolved in DMSO and added. The reaction was initiated by addition of HSF, incubated for 30 min at 37° C. and then stopped by addition of 2.5 ml of chloroform/methanol (1:1.5, v/v). The total lipids were extracted by the method of Bligh, E. G., and Dyer, W. J, Can. J. Biochem. Physiol. 37:911–917 (1959) by the further addition of 0.5 mL of chloroform and 1 mL of water with mixing. The lipid extract was redissolved in chloroform/methanol (9:1, v/v) containing 10 ug of carrier oleic acid. The oleic acid was separated from phospholipids by thin layer chromatography using gel-impregnated glass fiber sheets (ITLC type SG sheets). The sheets were preactivated by heating at 110° C. for 30 min. The lipid extract was applied to the sheets and chromatographed for 6 minutes, using hexane/acetic acid (100:1, v/v). The positions on the sheet containing oleic acid and phospholipids were visualized by exposure to iodine vapor and located by comparison to standards. The oleic acid and phospholipid zones were cut from the sheets, shaken individually with 2 ml of ethanol/water (80:20, v/v) and 15 ml of Aquasol, then counted for [$^{14}$C] radioactivity (dpm). PLA$_2$ activity, expressed as percent hydrolysis, was calculated from the formula:

$$\text{percent hydrolysis} = \frac{[^{14}C]\text{-oleic acid dpm}}{\{[^{14}C]\text{-oleic acid dpm} + [^{14}C]\text{-phospholipids dpm}\}} \times 100\%$$

and was corrected for nonenzymatic hydrolysis of the substrate. Percent inhibition due to the presence of drug was calculated from the formula:

$$\frac{\text{percent}}{\text{inhibition}} = \frac{(\text{Control Activity} - \text{Drug Activity})}{\text{Control Activity}} \times 100\%$$

When various concentrations of a Compound of Formula I were tested, the percent inhibition at each concentration was plotted as log concentration (abscissa) versus percent inhibition (ordinate) and the IC$_{50}$ was determined from this plot. Results are set forth in Table I.

II. Inhibition of Cellular Phospholipase A$_2$.- % Inhibition of Cellular PLA$_2$ Resident macrophages were obtained from rats by peritoneal lavage with phosphate buffered saline minus Ca$2^{++}$ and Mg$2^{++}$(PBS). Cells were washed 3 times with PBS and resuspended in Dulbecco's Modified Eagle's Medium (GiBco) containing L-glutamine low D-glucose (1000 mg/L), and sodium pyruvate (110 mg/L), supplemented with 10% fetal calf serum. Cells were counted on a Coulter ZBI cell counter and then resuspended to a concentration of 6×10$^6$ cells/1.5 ml. The cell suspension (1.5 ml culture dishes (35 mm) and the cells were allowed to adhere to the dishes for 90 minutes at 37° C. Dishes were washed 3 times with PBS to remove non-adherent cells. [$^{14}$C]arachidonic acid ([$^{14}$C]-AA, approximately 54 uCi/mmol, were added to the cells (1 uCi/dish) and allowed to incorporate for 120 minutes. Medium containing unincorporated [$^{14}$C]-AA was removed and the cell layer was again washed 3 times with PBS. Inhibitors were dissolved in dimethylsulfoxide (DMSO) and added directly to the macrophages in Hank's Balanced Salt Solution (GiBco) phosphate-buffered, pH 7.4) to obtain the desired final concentration. Cells were incubated with drug or DMSO for 30 minutes at 37° C. and were then stimulated with calcium-ionophore A-23187 (0.75 uM) for 20 minutes. The extracellular medium was removed and the [$^{14}$C] radioactivity released into this medium from AA metabolism was measured by liquid scintillation spectroscopy. The amounts of LTB$_4$ and PGE$_2$ were measured in the extracellular medium by radio immunoassay with specific antisera. The effects of inhibitor were measured as percent inhibition of A23187- stimulated AA metabolite release ($^{14}$C release, PGE$_2$ and LTB$_4$ production) (control) which were calculated from the formula:

$$\text{percent inhibition} = \frac{(\text{Control} - \text{Drug})}{\text{Control}} \times 100\%$$

IC$_{50}$'s were calculated as described in the HSF-PLA$_2$ assay. The results are set forth in Table I below:

TABLE 1

| | | IN VITRO Test results | |
|---|---|---|---|
| Ex No | Name | % Inhib. of HSF-PLA$_2$ at 5 μM [IC$_{50}$] in μM | % Inhib. of cellular PLA$_2$ at 5 μM [IC$_{50}$] μM3 |
| 43 | (E)-5-[2-(1,2,3,4-Tetrahydro-9-octyl-9H-dibenzo[pyrrol-6-yl)ethenyl]-2-furancarboxylic acid | 90a[6] | 100a[0.5] |
| 44 | (E)-5-[2-(1,2,3,4,-Tetrahydro-1,1-dimethyl-9-octyl-9H-dibenzo[b,d]pyrrol-6-yl)-ethenyl]-2-furancarboxylic acid | 71[2.5] | 62[4] |
| 45 | (E)-5-[2-(1,2,3,4-Tetrahydro-3,3-dimethyl-9-octyl-9H-dibenzo[b,d]pyrrol-6-yl)-ethenyl]-2-furancarboxylic acid | 86 | 53 |
| 46 | (E)-5-[2-(1,2,3,4-Tetrahydro-2,2,4,4-tetra-methyl-9-methyl-9H-dibenzo[b,d]pyrrol-6-yl]ethenyl]-2-furancarboxylic acid | 75 | 48 |
| 47 | (E)-5-[2-Methyl-2-(1,2,3,4-tetrahydro-9-octyl-9H-dibenzo[b,d]pyrrol-6-yl)-ethenyl]-2-furancarboxylic acid | 59 | 77 |
| 48 | (E)-5-[2-Methyl-2-(1,2,3,4-tetrahydro-1,1-dimethyl-9-octyl-9H-dibenzo[b,d]-pyrrol-6-yl)ethenyl]-2-furancarboxylic acid | 75 | 62 |
| 49 | (E)-5-[2-Methyl-2-(1,2,3,4-tetrahydro-2,2,4,4-tetramethyl-9-octyl-9H-dibenzo-[b,d]pyrrol-6-yl)ethenyl]-2-furancarboxylic acid | 83 | 15 |

TABLE 1-continued

IN VITRO Test results

| Ex No | Name | % Inhib. of HSF-PLA$_2$ at 5 μM [IC$_{50}$] in μM | % Inhib. of cellular PLA$_2$ at 5 μM [IC$_{50}$] μM3 |
|---|---|---|---|
| 50 | (E)-5-[1-Methyl-2-(1,2,3,4-tetrahydro-9-octyl-9H-dibenzo[b,d]pyrrol-6-yl) ethenyl]-2-furancarboxylic acid | 47 | 79 |
| 51 | (Z)-5-[2-(1,2,3,4-Tetrahydro-9-octyl-9H-dibenzo[b,d]pyrrol-6-yl)ethenyl]-2-furancarboxylic acid | 67[4] | 85[2] |
| 52 | (Z)-5-[2-(1,2,3,4-Tetrahydro-1,1-dimethyl-9-octyl-9H-dibenzo[b,d]pyrrol-6-yl)-ethenyl]-2-furancarboxylic acid | 73 | 66 |
| 53 | (E)-5-[1-Methyl-2-(1,2,3,4-tetrahydro-1,1-dimethyl-9-octyl-9H-dibenzo[b,d]-pyrrol-6-yl)ethenyl]-2-furancarboxylic acid | 73 | 63 |
| 55 | 5-[2-(1,2,3,4-Tetrahydro-9-octyl-9H-dibenzo[b,d]pyrrol-6-yl)ethyl]-2-furancarboxylic acid | 73 | 91 |
| 132 | 5-[(1,2,3,4-Tetrahydro-9-octyl-9H-dibenzo[b,d]pyrrol-6-yl)oxy]-2-furancarboxylic acid | 79[4] | 97[1] |
| 133 | 5-[(1,2,3,4-Tetrahydro-9-octyl-9H-dibenzo[b,d]pyrrol-7-yl)oxy]-2-furancarboxylic acid | 31 | 85 |
| 134 | 5-[(1,2,3,4-Tetrahydro-1,1-dimethyl-9-octyl-9H-dibenzo[b,d]pyrrol-6-yl)oxy]-2-furancarboxylic acid | 86 | 94 |
| 135 | 5-[(1,2,3,4-Tetrahydro-3,3-dimethyl-9-octyl-9H-dibenzo[b,d]pyrrol-6-yl)oxy]-2-furancarboxylic acid | 66 | 90 |
| 136 | 5-((1,2,3,4-Tetrahydro-9-butyl-9H-dibenzo[b,d]pyrrol-6-yl)oxy]-2-furancarboxylic acid | 12 | 85 |
| 137 | 5-[[1,2,3,4-Tetrahydro-9-(4-bromophenyl)methyl]-9H-dibenzo[b,d]pyrrol-6-yl]-oxy]-2-furancarboxylic acid | 36 | 100 |
| 138 | 5-[(1,2,3,4-Tetrahydro-9-methyl-9H-dibenzo[b,d]pyrrol-6-yl)oxy]-2-furancarboxylic acid | 39 | 13 |
| 139 | 5-[[1,2,3,4-Tetrahydro-9-(4-chlorophenyl)methyl]-9H-dibenzo[b,d]pyrrol-6-yl]-oxy]-2-furancarboxylic acid | 31 | 100 |
| 140 | 5-[(1,2,3,4-Tetrahydro-9-heptyl-9H-dibenzo[b,d]pyrrol-6-yl)oxy]-2-furancarboxylic acid | 55 | 97 |
| 141 | 5-[(1,2,3,4-Tetrahydro-9-dodecyl-9H-dibenzo[b,d]pyrrol-6-yl)oxy]-2-furancarboxylic acid | 66 | 74 |
| 142 | 5-[(1,2,3,4-Tetrahydro-9-nonyl-9H-dibenzo[b,d]pyrrol-6-yl)oxy]-2-furancarboxylic acid | 83 | 90 |
| 143 | 5-[[1,2,3,4-Tetrahydro-9-(4-heptylphenyl)methyl-9H-dibenzo[b,d]pyrrol-6-yl]-oxy]-2-furancarboxylic acid | 76 | 65 |
| 144 | rac-5-[[1,2,3,4-Tetrahydro-9-(3,7-dimethyl octyl)-9H-dibenzo[b,d]pyrrol-6-yl]oxy]-2-furancarboxylic acid | 78 | 87 |
| 145 | 5-[[1,2,3,4-Tetrahydro-9-(4-phenylbutyl)-9H-dibenzo[b,d]pyrrol-6-yl]oxy]-2-furancarboxylic acid | 47[4.8] | 99 |
| 146 | 5-[[1,2,3,4-Tetrahydro-9-[(4-fluor-ophenyl)methyl]-9H-dibenzo[b,d]pyrrol-6-yl]oxy]-2-furancarboxylic acid | 37 | 98 |
| 147 | 5-[[1,2,3,4-Tetrahydro-9-[(3-fluorophenyl)methyl]-9H-dibenzo[b,d]pyrrol-6-yl]oxy]-2-furancarboxylic acid | 37 | 94 |
| 148 | 5-[[1,2,3,4-Tetrahydro-9-[(2-fluorophenyl)methyl]-9H-dibenzo[b,d]pyrrol-6-yl]oxy]-2-furancarboxylic acid | 65 | 97 |
| 149 | 5-[[1,2,3,4-Tetrahydro-9-[(4-methoxyphenyl)methyl]-9H-dibenzo[b,d]pyrrol-6-yl]oxy]-2-furancarboxylic acid | 62 | 99 |
| 150 | 5-[[1,2,3,4-Tetrahydro-9-[(3,4-dimethoxy phenyl)methyl]-9H-dibenzo[b,d]pyrrol-6-yl]oxy]-2-furancarboxylic acid | 42 | 96 |
| 151 | 5-[[1,2,3,4-Tetrahydro-9-[(4-methylphenyl)methyl]-9H-dibenzo[b,d]pyrrol-6-yl]oxy]-2-furancarboxylic acid | 72[8 6] | 93 |
| 152 | 5-[[1,2,3,4-Tetrahydro-9-[(2,4,6-trimethyl phenyl)methyl]-9H-dibenzo[b,d]pyrrol-6-yl]oxy]-2-furancarboxylic acid | 72a | 89 |
| 153 | rac-5-[[1,2,3,4-Tetrahydro-1-(3-methoxy phenyl)-9-octyl-9H-dibenzo[b,d]pyrrol-6-yl]oxy]-2-furancarboxylic acid | 63[2.4] | 74 |
| 154 | rac-5-[(1,2,3,4-Tetrahydro-1,9-dioctyl-9H-dibenzo[b,d]pyrrol-6-yl)oxy]-2-furan carboxylic acid | 81 | 78 |
| 157 | 5-[(1,2,3,4-Tetrahydro-9-octyl-9H-dibenzo[b,d]pyrrol-6-yl)carbonyl]-2-furancarboxylic | 40 | 68 |

TABLE 1-continued

| | | IN VITRO Test results | |
|---|---|---|---|
| Ex No | Name | % Inhib. of HSF-PLA$_2$ at 5 μM [IC$_{50}$] in μM | % Inhib. of cellular PLA$_2$ at 5 μM [IC$_{50}$] μM3 |
| 160 | acid 5-[(1,2,3,4-Tetrahydro-9-octyl-9H-dibenzo [b,d]pyrrol-6-yl)methyl]-2-furancarboxylic acid[tz,1/44 | 49 | 94 | a: % Inhibition at 10 μM

III. Evaluation of the antiinflammatory activity of inhibitors

Inhibition of PLA$_2$- and carrageenan- induced paw edema in rats was used to evaluate the antiinflammatory activity of PLA$_2$ inhibitors.

A. PLA$_2$A -induced rat paw edema model of inflammation

Inhibitors were dissolved in DMSO for intraperitoneal administration, (i.p.) and in Labrafil M-19944CS for oral administration, (p.o.) 60 minutes prior to subplantar injection of PLA$_2$ (purified from Naja naja snake venom) dissolved in 100 ul saline, in the subplantar region of the right hind paw of male Lewis rats. Paw volume was measured using a water plethysmometer prior to PLA$_2$ injection (time 0) and then at 0.5, 1 and 4 hours there after. Controls received an equivalent amount of vehicle. Resulting paw edema was calculated by subtracting the initial paw volume from the paw volume recorded after PLA$_2$ injection. Statistical analysis of edema volume was performed using Students T-test. Percent inhibition was calculated from the formula:

$$\text{percent inhibition} = \frac{(\text{Control} - \text{Drug})}{\text{Control}} \times 100\%$$

B. Carrageenan-induced paw edema model of inflammation

Inhibitors were administered as described for (PLA$_2$ model) 60 minutes prior to subplantar injection of 0.1 ml 1% carrageenan dissolved in pyrogen free saline. Paw volume was measured as described above immediately prior to carrageenan injection and then at 1, 2, 4 and 6 hr thereafter. Controls received an equivalent amount of vehicle. Statistical analysis and percent inhibition were calculated as described for the PLA$_2$ model, above. The results are set forth in Table II below:

TABLE II

| | | IN VIVO- Test Results | | | |
|---|---|---|---|---|---|
| | | Carrageenan ind. paw edema | | PLA$_2$-ind. paw edema | |
| Ex-No | Name | dose mg/Kg | % Inhib. 2 hr | dose mg/Kg | % Inhib 2 hr |
| 43 | (E)-5-[2-(1,2,3,4-Tetrahydro-9-octyl-9H-dibenzo [bd]pyrrol-6-yl)ethenyl]-2-furancarboxylic acid | 50(ip) 100(po) | 40 29 | 50(ip) 100(po) | 60 NA |
| 44 | (E)-5-[2-(1,2,3,4,-Tetrahydro-1,1-dimethyl-9-octyl-9H-dibenzo[b,d]pyrrol-6-yl)-ethenyl]-2-furancarboxylic acid | 10(ip) 100(po) | 57 36 | 30(ip) 100(po) | 71 27 |
| 45 | (E)-5-[2-(1,2,3,4-Tetrahydro-2,2,4,4-tetramethyl-9-octyl-9H-dibenzo[b,d]pyrrol-6-yl] ethenyl]-2-furancarboxylic acid | 20(ip) | 46 | | |
| 47 | (E)-5-[2-Methyl-2-(1,2,3,4-tetrahydro-9-octyl-9H-dibenzo[b,d]pyrrol-6-yl)-ethenyl]-2-furancarboxylic acid | 20(ip) 100(po) | 70 49 | | |
| 48 | (E)-5-[2-Methyl-2-(1,2,3,4-tetrahydro-1,1-dimethyl-9-octyl-9H-dibenzo[b,d]-pyrrol-6-yl)ethenyl]-2-furancarboxylic acid | 10(ip) | 58 | | |
| 50 | (E)-5-[1-Methyl-2-(1,2,3,4-tetrahydro-9-octyl-9H-dibenzo[b,d]pyrrol-6-yl) ethenyl]-2-furancarboxylic acid | 20(ip) | 56 | | |
| 51 | (Z)-5-[2-(1,2,3,4-Tetrahydro-9-octyl-9H-dibenzo[b,d]pyrrol-6-yl)ethenyl]-2-furancarboxylic acid | 1(ip) 100(po) | 70 72 | | |
| 52 | (Z)-5-[2-(1,2,3,4-Tetrahydro-1,1-dimethyl-9-octyl-9H-dibenzo[b,d]pyrrol-6-yl)-ethenyl]-2-furancarboxylic acid | 10(ip) 100(po) | 50 NA | | |
| 53 | (E)-5-[1-Methyl-2-(1,2,3,4-tetrahydro- 1,1-dimethyl-9-octyl-9H-dibenzo[b,d]-pyrrol-6-yl)ethenyl]-2-furancarboxylic acid | 10(ip) 100(po) | 68 55 | | |
| 55 | 5-[2-(1,2,3,4-Tetrahydro-9-octyl-9H-dibenzo [b,d]pyrrol-6-yl)ethyl]-2-furancarboxylic acid | 10(ip) 100(po) | 59 49 | | |
| 132 | 5-[(1,2,3,4-Tetrahydro-9-octyl-9H-dibenzo [b,d]pyrrol-6-yl)oxy]-2-furancarboxylic acid | 3(ip) 100(po) | 45 65 | 100(po) | 34 |
| 133 | 5-[(1,2,3,4-Tetrahydro-9-octyl-9H-dibenzo [b,d]pyrrol-7-yl)oxy]-2-furancarboxylic acid | 100(po) | 58 | | |
| 134 | 5-[(1,2,3,4-Tetrahydro-1,1-methyl-9-octyl-9H-dibenzo[b,d]pyrrol-6-yl)oxy]-2-furancarboxylic acid | 20(ip) 100(po) | 36 48 | | |
| 136 | 5-[(1,2,3,4-Tetrahydro-9-butyl-9H-dibenzo [b,d]pyrrol-6-yl)oxy]-2-furancarboxylic acid | 30(ip) | NA | | |
| 138 | 5-[(1,2,3,4-Tetrahydro-9-methyl-9H-dibenzo | 30(ip) | NA | | |

TABLE II-continued

IN VIVO- Test Results

| Ex-No | Name | Carrageenan ind. paw edema | | PLA$_2$-ind. paw edema | |
|---|---|---|---|---|---|
| | | dose mg/Kg | % Inhib. 2 hr | dose mg/Kg | % Inhib. 2 hr |
| | [b,d]pyrrol-6-yl)oxy]-2-furancarboxylic acid | | | | |
| 139 | 5-[[1,2,3,4-Tetrahydro-9-(4-chlorophenyl) methyl-9H-dibenzo[b,d]pyrrol-6-yl]-oxy]-2-furancarboxylic acid | 30(ip) 100(po) | 68 NA | | |
| 140 | 5-[(1,2,3,4-Tetrahydro-9-heptyl-9H-dibenzo [b,d]pyrrol-6-yl)oxy]-2-furancarboxylic acid | 30(po) | NA | | |
| 141 | 5-[(1,2,3,4-Tetrahydro-9-dodecyl-9H-dibenzo [b,d]pyrrol-6-yl)oxy]-2-furancarboxylic acid | 30(po) | NA | | |
| 142 | 5-[(1,2,3,4-Tetrahydro-9-nonyl-9H-dibenzo [b,d]pyrrol-6-yl)oxy]-2-furancarboxylic acid | 30(po) | 48 | | |
| 143 | 5-[[1,2,3,4-Tetrahydro-9-(4-heptylphenyl) methyl-9H-dibenzo[b,d]pyrrol-6-yl]-oxy]-2-furancarboxylic acid | 30(po) | NA | | |
| 144 | rac-5-[[1,2,3,4-Tetrahydro-9-(3,7-dimethyl octyl)-9H-dibenzo[b,d]pyrrol-6-yl]oxy]-2-furancarboxylic acid | 30(ip) 100(po) | 80 NA | | |
| 145 | 5-[[1,2,3,4-Tetrahydro-9-(4-phenylbutyl)-9H-dibenzo[b,d]pyrrol-6-yl]oxy]-2-furancarboxylic acid | 30(ip) | 43 | | |
| 146 | 5-[[1,2,3,4-Tetrahydro-9-[(4-fluorophenyl) methyl]-9H-dibenzo[b,d]pyrrol-6-yl]oxy]-2-furancarboxylic acid | 30(ip) 100(po) | 51 33 | | |
| 147 | 5-[[1,2,3,4-Tetrahydro-9-[(3-fluorophenyl) methyl]-9H-dibenzo[b,d]pyrrol-6-yl]oxy]-2-furancarboxylic acid | 30(ip) | 49 | | |
| 149 | 5-[[1,2,3,4-Tetrahydro-9-[(4-methoxyphenyl) methyl]-9H-dibenzo[b,d]) pyrrol-6-yl]oxy]-2-furancarboxylic acid | 30(ip) | 48 | | |
| 150 | 5-[[1,2,3,4-Tetrahydro-9-[(3,4-dimethoxy phenyl)methyl]-9H-dibenzo[b,d]pyrrol-6-yl] oxy]-2-furancarboxylic acid | 30(ip) | 45 | | |
| 154 | rac-5-[(1,2,3,4-Tetrahydro-1,9-dioctyl-9H-dibenzo[b,d]pyrrol-6-yl)oxy]-2-furan carboxylic acid | 30(ip) 100(po) | 45 49 | | |
| 157 | 5-[(1,2,3,4-Tetrahydro-9-octyl-9H-dibenzo [b,d]pyrrol-6-yl)carbonyl]-2-furancarboxylic acid | 20(ip) 100(po) | 41 44 | | |
| 160 | 5-[(1,2,3,4-Tetrahydro-9-octyl-9H-dibenzo [b,d]pyrrol-6-yl)methyl]-2-furancarboxylic acid | 3(ip) 10(po) | 46 50 | 30(ip) | 49 |

NA - not active

IV. Adjuvant-induced Arthritis

Male Lewis rats (120–140 g) received 0.1 mg myeobacterium brityricum (0.5% ow/v) heavy mineral oil containing 0.2% digitonin administered in the base of the tail and the resulting arthritis was allowed to develop for 21 days (Coffey and Salvador, 1981). The combinded volumes of both hind paws were measured using a water plethysmograph by immersion of the paws to the level of the lateral malleolus. The animals were divided into drug-treated and vehicle (control) groups (six rats per group) with approximately equal volumes of both hind paws. On day 21, body weights were recorded and the i.p. or p.o. vehicle and drug were then administered daily for seven days. On day 28, the final day of the experiment, heparinized (0.2 units/100 μl) blood was also collected for measurement of plasma fibrinogen concentrations (Goodwin, 1961). The changes in paw volume and body weight were calculated as paw volume or body weight at day 28 minus paw volume or body weight at day 21. Values are reported as means ± S.E. for n=6. Plasma fibrinogen concentration was quantitated according to Goodwin et al. (1961) and is expressed in mg/dl. Statistical differences between measurement parameters of the drug-treated and control groups were determined using Students's t-test. The results are set forth in Table III below:

TABLE III

| | | Established-adjuvant arthritis test | | |
|---|---|---|---|---|
| Ex No | Name | dose mg/Kg | Change of paw volume (vehicle) mL | body wt. (vehicle) g |
| 43 | (E)-5-[2-(1,2,3,4-Tetrahydro-9-octyl-9H-dibenzo [b,d]pyrrol-6-yl)ethenyl]-2-furancarboxylic acid | 10(ip) 100(po) | −0.18(0.39) −0.29(0.23) | 12(13) 12(15) |
| 44 | (E)-5-[2-(1,2,3,4,-Tetrahydro-1,1-dimethyl-9-octyl-9H-dibenzo[b,d]pyrrol-6-yl)-ethenyl]-2-furancarboxylic acid | 30(po) | 0.68(1.13) | 5(10) |
| 45 | (E)-5-[2-(1,2,3,4-Tetrahydro-2,2,4,4-tetra-methyl-9-octyl-9H-dibenzo[b,d]pyrrol-6-yl] ethenyl]-2-furancarboxylic acid | 50(po) | NA | |
| 51 | (Z)-5-[2-(1,2,3,4-Tetrahydro-9-octyl-9H- | 10(po) | 0.71(1.25) | 6(12) |

TABLE III-continued

| | | Established-adjuvant arthritis test | | |
|---|---|---|---|---|
| Ex No | Name | dose mg/Kg | Change of paw volume (vehicle) mL | body wt. (vehicle) g |
| 52 | dibenzo[b,d]pyrrol-6-yl)ethenyl]-2-furancarboxylic acid (Z)-5-[2-(1,2,3,4-Tetrahydro-1,1-dimethyl-9-octyl-9H-dibenzo[b,d]pyrrol-6-yl)-ethenyl]-2-furancarboxylic acid | 30(po) | 0.66(1.25) | 13(12) |
| 132 | 5-[(1,2,3,4-Tetrahydro-9-octyl-9H-dibenzo[b,d]pyrrol-6-yl)oxy]-2-furancarboxylic acid | 10(po) | 0.48(1.00) | 13(13) |
| 136 | 5-[(1,2,3,4-Tetrahydro-9-butyl-9H-dibenzo[b,d]pyrrol-6-yl)oxy]-2-furancarboxylic acid | 30(po) | NA | |
| 154 | rac-5-[(1,2,3,4-Tetrahydro-1,9-dioctyl-9H-dibenzo[b,d]pyrrol-6-yl)oxy]-2-furan carboxylic acid | 30(po) | NA | 10(7) |
| 160 | 5-[(1,2,3,4-Tetrahydro-9-octyl-9H-dibenzo[b,d]pyrrol-6-yl)methyl]-2-furancarboxylic acid | 30(po) | 0.47(1.2) | 4(9) |

REFERENCES

Hope, W. C., Patel, B. J., Fiedler-Nagy, C., and Wittreich, B. H. (1990) Retinoids inhibit phospholipase $A_2$ in human synovial fluid and arachidonic acid release from rat peritoneal macrophages. Inflammation 14: 543–559.

Coffey, J. W., and Salvador, R. A. (1981) Levels of collagenolytic activity, $\beta$-glucuronidase and collagen prolyl hydroxylase in paws from rats with developing adjuvant arthritis. Biochim. Biophys. Acta 667: 243–252.

Goodwin, J. R. (1961) Estimation of plasma fibrinogen, using sodium sulfite fractionation. Am. J. Clin. Pathol. 35: 227–232.

In practice of the invention, the dose of a compound of formula I or a salt thereof to be administered and the frequency of administration will be dependent on the potency and duration of activity of the particular compound of formula I or salt to be administered and on the route of administration, as well as the severity and nature of the condition and age of the mammal to be treated and the like. Oral doses of a compound of formula I or a salt thereof contemplated for use in practicing the invention can be in range of from 10 mg to about 2.0 g per day, preferably about 50 mg to about 1 g per day, either as a single does or in divided doses. For topical use as a compound of formula I or salt thereof contemplated for use in practicing the invention is present in the topical composition in the range of from about 1 to about 10%, preferably from about 2 to about 5%.

A compound of formula I, or a salt or a composition containing a therapeutically effective amount of a compound of formula I, or a salt thereof can be administered by methods well known in the art. Thus, a compound of formula 1, or a salt thereof can be administered either singly or with other pharmaceutical agents, for example, antihistamines, metdiator release inhibitors, methyl xanthines, beta agonists or antiasthmatic steroids such as prednisone and prednisolone, orally, parenterally, rectally, or by inhalation, for example in the form of an aerosol, micropulverized powder or nebulized solution. For oral administration, they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered as solutions or suspension, for example, as an aqueous or peanut oil suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in pressurized container fitted with an aerosol valve suitable for release of the pressurized composition. Preferably, the aerosol valve is a metered valve, that is one which on activation releases a predetermined effective dose of the aerosol composition. For topical use, they can conveniently be used in the form of salves, tinctures, creams, solutions, lotions, sprays, suspensions and the like. Salves and creams as well as solutions are preferred. These topical preparations can be prepared by mixing a compound of formula 1 as an active ingredient with one or more non-toxic, inert, solid or liquid carriers which are usual in such preparations and which are suitable for topical treatment.

The examples which follow further illustrated the invention. All temperatures given are in degree centigrade. Melting points were taken on a Thomas Hoover capillary melting point apparatus and are uncorrected. All reactions were carried out under an inert gas. All compounds for testing have been prepared in a chemically pure form and were compatible with $^1$H-NMR, IR, UV, MS data. Proton Magnetic Resonance Spectra (1H-NMR) were taken on a Varian XL-200 or XL-400 spectrometer and electron impact or fast bombardment mass spectra were taken on either VG ZAB-1F or VG 70E-HF mass spectrometers. Purification of the compounds was performed on silica gel chromatographic column or preparative high pressure liquid chromatography (HPLC) on a Waters Associates Prep LC 500A using silica gel Prep-Pack 500 cartridges.

EXAMPLES

In the examples which follow, all temperatures are in degree centigrade. Melting points were taken on a Thomas Hoover capillary melting point apparatus and are uncorrected. All reactions were carried out under an inert gas. All compounds for testing have been prepared in a chemically pure form and were compatible with $^1$H-NMR, IR, UV, MS data. Proton Magnetic Resonance Spectra (1H-NMR) were taken on a Varian XL-200 or XL-400 spectrometer and electron impact or fast bombardment mass spectra were taken on either VG ZAB-1F or VG 70EHF mass spectrometers. Purification of the compounds was performed on silica gel chromatographic column or preparative high pressure liquid chromatography (HPLC) on a Waters Associates Prep LC 500A using silica gel Prep-Pack 500 cartridges.

EXAMPLE 1

Preparation of 5,6,7,8-tetrahydro-9H-dibenzo[b,d]pyrrole-3-carboxylic acid ethyl ester A mixture of 52.0 g of 6-carbethoxyphenylhydrazine hydrochloride and 25.9 g of cyclohexanone in 250 ml of 80% aqueous acetic acid was refluxed for 5 hours. The reaction was cooled, poured into water and extracted with ethyl acetate. The combined extracts were washed with additional water, dried over anhydrous magnesium sulfate, filtered and concentrated in vacuo to give 56.0 g of an orange semisolid material which, after crystallization from ethyl acetate-hexane, afforded 35.9 g (61.5%) of 5,6,7,8-tetrahydro-9H-dibenzo[b,d]pyrrole-3-carboxylic acid ethyl ester as a yellow solid.

EXAMPLE 2

Preparation of 5.6.7,8-tetrahydro-9H-dibenzo[b,d]pyrrole-3-carbonitrile

Using the procedure of Example 1, 30.0 g of 4-hydrazinobenzonitrile monohydrochloride was reacted with 18.0 g of cyclohexanone in 100 ml of 80% aqueous acetic acid giving 23.8 g (68%) of 5,6,7,8-tetrahydro-9H-dibenzo[b,d]pyrrole-3-carbonitrile as a grey solid after purification on a silica gel column.

EXAMPLE 3

Preparation of 2,2-dimethylcyclohexanone

To a stirring solution of 25.1 g of isobutyronitrile and 61.0 g of 2-(2-bromoethyl)-1,3-dioxolane in 300 ml of anhydrous ether was slowly added 310 ml of a 1.5M solution of lithiumdiisopropylamide mono(tetrahydrofuran) in cyclohexane at 0°-5° C. After removal of the cooling bath, the reaction mixture was stirred for 4 hours at room temperature, treated with a saturated solution of ammonium chloride and worked up with ether. The organic phase was washed with water, dried over anhydrous magnesium sulfate and concentrated to give 61 g of a crude oil. Purification of this material on a silica gel column (eluting system:ether-hexane 4:1) afforded 47.9 g (77.9%) of α, α-dimethyl-1,3-dioxolane-2-butanenitrile. A solution of 47.9 g of α,α-dimethyl-1,3dioxolane-2-butanenitrile in 500 ml of anhydrous ethyl ether was treated with 200 ml of 1.4M methyllithium solution in ether at 0°-5° C. The reaction mixture was stirred for 2 hours at room temperature, treated with a saturated ammonium chloride solution and worked up with ether. The ethereal solution was washed with water, dried over anhydrous magnesium sulfate and concentrated in vacuo to give 39.2 g of a crude yellow oil. This material was treated with 70 ml of 4N-sulfuric acid and refluxed for 13 hours. After being cooled, the mixture was extracted with ether. The organic phase was washed with water, a saturated solution of sodium bicarbonate, water, dried over anhydrous magnesium sulfate and concentrated to give 23.1 g (65.8%) of 6,6-dimethyl-2-cyclohexen-1-one as an orange oil. This material was used without further purification.

Hydrogenation of 23.1 g of this material over 0.7 g of 10% palladium on carbon in 230 ml of ethyl acetate, at atmospheric pressure and room temperature afforded 22.1 g (94.1%) of 2,2-dimethylcyclohexanone after filtration of the catalyst, solvent evaporation and distillation at 45°–50° C./12 mmHg.

EXAMPLE 4

Preparation of 5,6,7,8-tetrahydro-8,8-dimethyl-9H-dibenzo[b,d]pyrrole-3-carboxylic acid ethyl ester Using the procedure of Example 1, the reaction of 29.0 g of 6-carbethoxyphenylhydrazine hydrochloride with 16.9 g of 2,2-dimethylcyclohexanone in 250 ml of 80% aqueous acetic acid afforded 21.1 g (58%) of 1,2,3,4-tetrahydro-1,1-dimethyl-9H-dibenzo [b,d]pyrrole-6-carboxylic acid ethyl ester as an orange solid after chromatographic purification.

EXAMPLE 5

Preparation of 5,6,7,8-tetrahydro-8,8-dimethyl-9H-dibenzo[b,d]-pyrrole3-carbonitrile Using the procedure of Example 1, 12.0 g of 4-hydrazinobenzonitrile monohydrochloride and 9.05 g of 2,2-dimethyl-cyclohexanone in 100 mL of 80% aqueous acetic acid gave 4.6 g (30.5%) of 5,6,7,8-tetrahydro-8,8-dimethyl-9H-dibenzo[b,d]pyrrole-3-carbonitrile as a white solid after chromatographic purification.

EXAMPLE 6

Preparation of 5,6,7,8-tetrahydro-6,6-dimethyl-9H-dibenzo[b,d]pyrrole-3-carboxylic acid ethyl ester Using the procedure of Example 1, 5.7 g of 6-carbethoxyphenylhydrazine hydrochloride was reacted with 3.3 g of 4,4-dimethylcyclohexanone in 60 mL of 80% aqueous acetic acid to give 4.8 g (67%) of 5,6,7,8-tetrahydro-6,6-dimethyl-9H-dibenzo[b,d]pyrrole-3-carboxylic acid ethyl ester after crystallization from ethyl acetate-hexane.

EXAMPLE 7

Preparation of 5,6,7,8-tetrahydro-5,5,7,7-tetramethyl-9H-dibenzo [b,d]pyrrole-3-carboxylic acid ethyl ester Using the procedure of Example 1, 9.0 g of 6-carbethoxyphenylhydrazine hydrochloride was reacted with 6.45 g of 3,3,5,5-tetramethylcyclohexanone in 100 ml of 80% aqueous acetic acid giving 2.2 g (17.5%) of 5,6,7,8-tetrahydro-5,5,7,7-tetramethyl-9H-dibenzo[b,d]pyrrole-3-carboxylic acid ethyl ester as an orange solid after chromatographic purification.

EXAMPLE 8

Preparation of 5,6,7,8-tetrahydro-5,5,7,7-tetramethyl-9H-dibenzo[b,d]pyrrole-3-carbonitrile Using the procedure described in Example 1, 8.0 g of 4-hydrazinobenzonitrile monohydrochloride and 7.3 g of 3,3,5,5-tetramethylcyclohexanone in 80 mL of 80% aqueous acetic acid produced 1.1 g (11%) of 5,6,7,8-tetrahydro-5,5,7,7-tetramethyl-9H-dibenzo[b,d]pyrrole-3-carbonitrile as a yellow oil, after chromatographic purification.

EXAMPLE 9

Preparation of 5,6,7,8-tetrahydro-9-octyl-9H-dibenzo[b,d]pyrrole-3-carboxylic-acid ethyl ester A mixture of 35.9 g of 1,2,3,4-tetrahydro-9H-dibenzo[b,d]pyrrole-6-carboxylic acid ethyl ester from Example 1, 14.9 g of sodium hydroxide, 1.7 g of tetrabutylammonium bromide, 28 ml of 1-bromooctane in 325 ml of dried toluene was refluxed for 4 hours. The reaction mixture was cooled, diluted with water, acidified with 2N-HCl (pH=1) and extracted with ethyl acetate. The organic extracts were washed with water, dried over anhydrous magnesium sulfate and concentrated in vacuo giving 60.1 g of an orange oil. Chromatographic purification of this material (silica gel, eluent: hexane) gave 48.3 g (92.1%) of 5,6,7,8-tetrahydro-9-octyl-9H-dibenzo[b,d]pyrrole-3-carboxylic acid ethyl ester as a yellow oil.

EXAMPLE 10

Preparation of 5,6,7,8-tetrahydro-9-octyl-9H-dibenzo[b,d,]pyrrole-3-carbonitrile Using the procedure described in Example 9, 10.2 g of the carbonitrile from Example 2 was alkylated with 12.8 g of 1-bromooctane to give 11.5 g (68.5%) of 5,6,7,8-tetrahydro-9-octyl-9H-dibenzo[b,d]pyrrole-3-carbonitrile as a white solid.

EXAMPLE 11

Preparation of 5,6,7,8-tetrahydro-8,8-dimethyl-9-octyl-9H-dibenzo[b,d]pyrrol-3-carboxylic acid ethyl ester Using the procedure of Example 9, 21.1 g of the ester from Example 4 was alkylated with 19.3 g of 1-bromooctane to provide 19.0 g (63.7%) of 5,6,7,8-tetrahydro-8,8-dimethyl-9-octyl-9H-dibenzo[b,d]pyrrole-3-carboxylic acid ethyl ester as a yellow oil after purification on a chromatographic column of silica gel.

EXAMPLE 12

Preparation of 5,6,7,8-tetrahydro-8,8-dimethyl-9-octyl-9H-dibenzo[b,d]pyrrole-3-carbonitrile Using the procedure of Example 9, 5.6 g of the carbonitrile from Example 5 was alkylated with 6.35 g of 1-bromooctane to give 9.1 g (96.4%) of 5,6,7,8-tetrahydro-8,8-dimethyl-9-octyl-9H-dibenzo[b,d]pyrrole-3-carbonitrile as a yellow oil. This material was used without purification.

EXAMPLE 13

Preparation Of 5,6,7,8-tetrahydro-6,6-dimethyl-9-octyl-9H-dibenzo[b,d]pyrrole-3-carboxylic acid ethyl ester Using the procedure of Example 9, 4.8 g of the ethyl ester from Example 6 was alkylated with 4.38 g of 1-bromooctane to provide 5,6,7,8-tetrahydro-6,6-dimethyl-9-octyl-9H-dibenzo[b,d]pyrrole-3-carboxylic acid ethyl ester (7.0 g;100%) as a yellow oil after purification on a small pad of silica gel.

EXAMPLE 14

Preparation of 5,6,7,8-tetrahydro-5,5,7,7-tetramethyl-9-octyl-9H-dibenzo[b,d]pyrrole-3-carboxylic acid ethyl ester Using the procedure of Example 9, 2.2 g of the ethyl ester from Example 7 was alkylated with 1.83 g of 1-bromooctane to give 5,6,7,8-tetrahydro -5,5,7,7-tetramethyl-9-octyl-9H-dibenzo[b,d]pyrrole-3-carboxylic acid ethyl ester (2.3 g; 76.1%) as an orange oil after chromatographic purification.

EXAMPLE 15

Preparation of 5,6,7,8-tetrahydro-5,5,7,7-tetramethyl-9-octyl-9H-dibenzo[b,d]pyrrole-3-carbonitrile Using the procedure of Example 9, 1.1 g of the carbonitrile from Example 8 was alkylated with 1.16 g of 1-bromooctane to give 5,6,7,8-tetrahydro -5,5,7,7-tetramethyl-9-octyl-dibenzo[b,d]pyrrole-3-carbonitrile (1.3 g; 82.5%) as a yellow oil after chromatographic purification.

EXAMPLE 16

Preparation of 5,6,7,8-tetrahydro-9-octyl-9H-dibenzo[b,d]pyrrole-3methanol

A solution of 30.4 g of 5,6,7,8-tetrahydro-9-octyl-9H-dibenzo[b,d]pyrrole-3-carboxylic acid ethyl ester from Example 9, in 300 ml of methylene chloride was treated with 124 ml of a 1.5M DIBAH solution in toluene at 0°–5° C. (ice-water bath) in approximately 20 minutes. After an additional 20 minutes stirring at the same temperature, the reaction mixture was cautiously poured into cold 2N-HCl ice and extracted with methylene chloride. The organic extracts were washed with water and brine, then dried over anhydrous magnesium sulfate, filtered and concentrated in vacuo to give 28.3 g of a crude yellow oil. Purification of this material on a small silica gel pad (eluting system:hexane-ethyl acetate 1:1) produced 25.8 g (96.2%) of 5,6,7,8-tetrahydro-9-octyl-9H-dibenzo[b,d]pyrrole-3-methanol as a yellow oil.

EXAMPLE 17

Preparation of 5,6,7,8-tetrahydro-8,8-dimethyl-9-octyl-9H-dibenzo[b,d]pyrrole-3-methanol Using the procedure of Example 16, 19.0 g of the ethyl ester from Example 11 was reduced to 5,6,7,8-tetrahydro-8,8-dimethyl-9-octyl-9H -dibenzo[b,d]pyrrole-3-methanol (16.2 g; 95.5%) as an orange oil. This material was used without purification.

EXAMPLE 18

Preparation Of 5,6,7,8, tetrahydro-6.6-dimethyl-9-octyl-9H-dibenzo[b,d]pyrrole-3-methanol Using the condition described in Example 16, 4.6 g of the ethyl ester from Example 13 was reduced to 5,6,7,8-tetrahydro-6,6-dimethyl9-octyl-9H-dibenzo[b,d]pyrrole-3-methanol (3.9 g; 95%) as a yellow oil after purification on a small pad of silica gel.

EXAMPLE 19

Preparation Of 5,6,7,8-tetrahydro-5,5,7,7-tetramethyl-9-octyl-9H-dibenzo[b,d]pyrrole-3-methanol Using the procedure of Example 16, 2.3 g of the ethyl ester from Example 14 was reduced to 5,6,7,8-tetrahydro-5,5,7,7-tetramethyl-9-octyl-9H-dibenzo[b,d]pyrrole-3-methanol (1.3 g; 63.1%) as a yellow oil after chromatographic purification.

EXAMPLE 20

Preparation of 5,6,7,8-tetrahydro-9-octyl-9H-dibenzo[b,d]pyrrole-3-carboxaldehyde Using the procedure of Example 16, 7.6 g of 5,6,7,8-tetrahydro-9-octyl-9H-dibenzo[b,d]pyrrole-3-carbonitrile from Example 10 was converted to the corresponding 5,6,7,8-tetrahydro-9-octyl-9H-dibenzo[b,d]pyrrole-3-carboxaldehyde (6.8 g; 89.0%) as a yellow oil after purification on a small silica gel pad.

EXAMPLE 21

Preparation of 5,6,7,8-tetrahydro-8,8-dimethyl-9-octyl-9H-dibenzo[b,d]pyrrole-3-carboxaldehyde Using the procedure from Example 16, 4.1 g of the carbonitrile from Example 12 was converted to 5,6,7,8-tetrahydro-8,8-dimethyl-9- octyl-9H-dibenzo[b,d]pyrrole-3-carboxaldehyde. (3.8 g; 92.0%) as a yellow oil after purification on a small pad of silica gel.

EXAMPLE 22

Preparation of 5,6,7,8,tetrahydro-5,5,7,7-tetramethyl-9-octyl-9H-dibenzo[b,d]pyrrole-3-carboxaldehyde Using the procedure described in Example 16, 1.3 g of the carbonitrile from Example 15 was converted into 5,6,7,8-tetrahydro-5,5,7,7-tetramethyl-9-octyl-9H-dibenzo-[b,d]pyrrole-3-carboxaldehyde (1.2 g; 94.5%) as a yellow oil after purification on a small pad of silica gel.

EXAMPLE 23

Preparation of 5,6,7,8-tetrahydro-α-methyl-9-octyl-9H-dibenzo[b,d]pyrrole-3-methanol A solution of 4.5 g of 5,6,7,8-tetrahydro-9-octyl-9H-dibenzo[b,d]pyrrole-3-carboxaldehyde from Example 20 in 40 ml of dried tetrahydrofuran was treated with 5.2 mL of a 3M solution of methylmagnesium bromide in ether at 0°–5° C. The reaction mixture was stirred at the same temperature for 1 hour, poured into a saturated solution of ammonium chloride and extracted with ether. The ethereal extracts were washed with water, dried over anhydrous magnesium sulfate and concentrated to give 4.8 g of crude alcohol as a yellow oil. This material was chromatographed on a silica gel column (eluting system: hexane-ethyl acetate 2:1) giving 4.3 g (91%) of 5,6,7,8-tetrahydro-α-methyl-9-octyl-9H-dibenzo[b,d]pyrrole-3-methanol as a yellow oil after chromatographic purification.

EXAMPLE 24

Preparation of 5,6,7,8-tetrahydro-α-methyl-8,8-dimethyl-9-octyl-9H-dibenzo[b,d]pyrrole-3-methanol Using the procedure of Example 23, 2.0 g of the carboxaldehyde from Example 21 was converted into 5,6,7,8-tetrahydro-α-methyl-8,8-dimethyl -9-octyl-9H-dibenzo[b,d]pyrrole-3-methanol (1.5 g; 71.5%) as a yellow oil after chromatographic purification.

EXAMPLE 25

Preparation of 5,6,7.8-tetrahydro-α, 5,5,7,7-pentamethyl-9-octyl-9H-dibenzo[b,d]pyrrole-3-methanol Using the procedure of Example 23, 1.2 g of the carboxaldehyde from Example 22 was converted into 5,6,7,8-tetrahydro-a, 5,5,7 7-pentamethyl -9-octyl-9H-dibenzo[b,d]pyrrole-3-methanol (0.53 g; 42.2%) as a yellow oil after chromatographic purification.

EXAMPLE 26

Preparation of triphenyl-[(1,2,3,4-tetrahydro-9-octyl-9H-dibenzo[b,d]pyrrol-6-yl)methyl]phosphonium bromide A solution of 25.8 g of 5,6,7,8-tetrahydro-9-octyl-9H-dibenzo[b,d]pyrrole-3-methanol obtained as described in Example 16, and 28.3 g of triphenylphosphine hydrobromide in 280 ml of toluene was refluxed for 90 minutes. The reaction mixture was concentrated to give a yellow viscous material, which crystallized upon heating with a small amount of ethyl acetate. The precipitate was collected and dried to give 19.8 g (37.6%) of the corresponding phosphonium salt as a white solid.

EXAMPLE 27

Preparation of triphenyl-[(1,2,3,4tetrahydro-1-dimethyl-9-octyl-9H-dibenzo[b,d]pyrrol-6-yl)methyl]phosphonium bromide A mixture of 16.2 g of 5,6,7,8-tetrahydro-8,8-dimethyl-9-octyl-9H-dibenzo[b,d]pyrrole-3-methanol from Example 17, 16.2 g of triphenylphosphine hydrobromide in 160 ml of methylene chloride was stirred for 17 hours at room temperature. After removal of the solvent, the residual yellow foam was triturated with ethyl acetate and ether until a precipitate was formed. The solvent was decanted and the solid dried to give 17.8 g (56%) of the corresponding phosphonium salt as a light green material.

EXAMPLE 28

Preparation of triphenyl-[(1,2,3,4-tetrahydro-3,3-dimethyl-9octyl-9H-dibenzo[b,d]pyrrol-6-yl)methyl]-phosphonium bromide Using the procedure of Example 26, 3.9 g of alcohol from Example 18 was converted into the corresponding phosphonium salt (5.9 g) in 77.5% yield as a white solid.

EXAMPLE 29

Preparation of triphenyl-[(1,2,3, 4-tetrahydro-2,2,4,4-tetramethyl-9-octyl-9H-dibenzo[b,d]pyrrol-6-yl)methyl]phosphonium bromide Using the procedure of Example 26, 1.3 g of 5,6,7,8-tetrahydro-2,2,4,4-tetramethyl-9-octyl-9H-dibenzo[b,d]pyrrole-3-methanol from Example 19 was converted into the corresponding phosphonium salt (2.2 g; 90.1%) as a pale yellow solid.

EXAMPLE 30

Preparation of triphenyl-[1-(1,2,3,4-tetrahydro-2,2,4,4-tetramethyl-9octyl-9H-dibenzo[b,d]pyrrol-6-yl)ethyl]-phosphonium bromide Using the procedure described in Example 27, 3.6 g of 5,6,7,8-tetrahydro -a-methyl-9-octyl-9H-dibenzo[b,d]pyrrole-3-methanol from Example 23 was converted into the corresponding phosphonium salt (6.7 g) in 92% yield as a white foam. The material was used without purification.

EXAMPLE 31

Preparation of triphenyl-[1-(1,2,3,4-tetrahydro-1,1-dimethyl-9-octyl-9H-dibenzo[b,d]pyrrol-6-yl)ethyl]-phosphonium bromide Using the procedure described in Example 27, 1.5 g of alcohol from Example 24 was converted into the corresponding phosphonium salt (2.5 g; 78.0%) as a pale yellow solid.

EXAMPLE 32

Preparation of triphenyl-[1-(1,2,3,4-tetrahydro-2,2,4,4-tetramethyl-9-octyl-9H-dibenzo[b,d]-pyrrol-6yl)ethyl]-phosphonium bromide Using the procedure of Example 27, 0.53 g of 5,6,7,8-tetrahydro-α, 5,5,7,7-pentamethyl-9-octyl-9H-dibenzo[b,d]pyrrole-3-methanol from Example 25 was converted into the corresponding phosphonium salt (0.94 g; 96%) as a yellow solid.

EXAMPLE 33

Preparation of(E)-5-[2-(1,2,3,4-tetrahydro-9-octyl-9H-dibenzo[b,d]pyrrole-6-yl)ethenyl]-2-furancarboxylic acid methyl ester and (Z)-isomer analog A solution of 15.8 g of the phosphonium salt from Example 26 and 4.1 g of 5-formyl-2-furancarboxylic acid methyl ester in 100 ml of methylene chloride was cooled at —50° C. At this temperature, 17.4 ml of a 1.6M sodium methoxide in methanol solution was slowly added. After being stirred at —50° C. for 15 minutes and 3 hours at room temperature, the reaction mixture was poured into water and extracted with methylene chloride. The organic phase was washed with additional water, dried over anhydrous magnesium sulfate and concentrated in vacuo to give 20.5 g of an orange oil, as a mixture of trans-cis isomers in approximately 3:1 ratio. This material was passed through a short pad of silica gel (eluting system:hexane-ethyl acetate 2:1) producing 13.6 g of a yellow oil. Careful chromatography of this material on a silica gel column (eluting system: hexane-ethyl acetate 9:1) afforded 6.5 g (60.7%) of (E)-5-[2-(1,2,3,4-tetrahydro-9-octyl-9H-dibenzo[b,d]pyrrole-6-yl)ethenyl]-2-furancarboxylic acid methyl ester and 1.7 g (15.8%) of the corresponding (Z)-isomer both as yellow oils.

EXAMPLE 34

Preparation of (E)-5-[2-(1,2,3,4-tetrahydro-1, dimethyl-9-octyl-9H-dibenzo[b,d]pyrrol-6-yl)-ethenyl]-2-furancarboxylic acid methyl ester and (Z)-isomer analog Using the procedure of Example 33, 17.8 g of phosphonium salt from Example 27, was converted into (E)-5-[2-(1,2,3,4-tetrahydro-1,1-dimethyl -9-octyl-9 H-dibenzo[b,d,]pyrrol-6-yl )ethenyl]-2-furancarboxylic acid methyl ester (5.5 g) in 45% yield and 2.4 g of the (Z) isomer in 20% yield, both as orange oils after careful chromatographic purification.

EXAMPLE 35

Preparation of (E)-5-[2-(1,2,3,4-tetrahydro-3,3-dimethyl-9-octyl-9H-dibenzo[b,d]pyrrol-6-yl)ethenyl]-2-furancarboxylic acid methyl ester Using the procedure described in Example 33, 5.9 g of the phosphonium salt from Example 28 was converted into (E)-5-[2-(1,2,3,4-tetrahydro-3,3-dimethyl-9-octyl-9H-dibenzo[b,d]pyrrol-6-yl)ethenyl]-2-furancarboxylic acid methyl ester (2.1 g; 51.5%) as a yellow oil after chromatographic purification.

EXAMPLE 36

Preparation of (E)-5-[2-(1,2,3,4-tetrahydro-2,2,4,4-tetramethyl-9-octyl-9H-dibenzo[b,d]pyrrol-6-yl)ethenyl]-2-furnancarboxylic acid methyl ester Using the procedure described in Example 33, 2.2 g of the phosphonium salt from Example 29 was converted into (E,Z)-5-[2-(1,2,3,4-tetrahydro-2,2,4,4-tetramethyl-9-octyl-9H-dibenzo[b,d]pyrrol6-yl)ethenyl]-2-furancarboxylic acid methyl ester. The (E)-isomer (0.8 g) was obtained in 51.6% yield as a yellow oil by purification of the isomeric mixture on a chromatographic silica gel column.

EXAMPLE 37

Preparation of (E)-5-[2-methyl-2-(1,2,3,4-tetrahydro-9-octyl-9H-dibenzo[b,d]pyrrol-6-yl)-ethenyl]-2-furancarboxylic acid methyl ester To a slurry of 1.4 g of the phosphonium salt obtained from Example 30 in 10 ml of tetrahydrofuran, 1.35 ml of 1.6M n-buthyllithium solution in hexane was added at 0°–5° C. The reaction mixture was stirred at room temperature for 1 hour and then cooled to −50° C. At this temperature a solution of 0.4 g of 5-formyl-2-furancarboxylic acid methyl ester in 1 mL of tetrahydrofuran was added. The new mixture was stirred 15 minutes at −50° C., 2 hours at room temperature, poured into water and brine and extracted with methylene chloride. The organic phase was washed with water, dried over anhydrous magnesium sulfate and concentrated to give 1.6 g of an orange oil. Purification of this material on a chromatographic column (eluting system:hexane-ethyl acetate 4:1) afforded 0.756 g (75.5%) of (E)-5-[2-methyl-2-(1,2,3,4-tetrahydro-9-octyl-9H-dibenzo[b,d]pyrrol-6-yl)ethenyl]-2-furancarboxylic acid methyl ester as a yellow oil.

EXAMPLE 38

Preparation of (E)-5-[2-methyl-2-(1,2,3,4-tetrahydro-1,1-dimethyl-9-octyl-9H-dibenzo[b,d]-pyrrol-6-yl)ethenyl]-2-furancarboxylic acid methyl ester Using the procedure described in Example 37, 2.0 g. of the phosphonium salt from Example 31 was converted into (E)-5-[2-methyl -2-(1,2,3,4-tetrahydro-1,1-dimethyl-9-octyl-9H-dibenzo[b,d]pyrrol-6-yl)ethenyl]-2-furancarboxylic acid methyl ester (0.7 g; 66.8%) as a yellow oil after chromatographic purification.

EXAMPLE 39

Preparation of (E)-5-[2-methyl-2-(1,2,3,4-tetrahydro-2,2,4,4-tetramethyl-9-octyl-9H-dibenzo-[b,d]pyrrol-6,yl)ethenyl]-2-furancarboxylic acid methyl ester Using the procedure of Example 37, 0.94 g of the phosphonium salt from Example 32 was condensed with 0.225 g of 5-formyl-2-furancarboxylic acid methyl ester giving 0.57 g of (E)-5-[2-methyl-2-(1,2,3,4-tetrahydro-2,2,4,4-tetramethyl-9-octyl-9H-dibenzo[b,d]pyrrol6-yl)ethenyl]-2-furancarboxylic acid methyl ester in 85% yield as a yellow oil after chromatographic purification.

EXAMPLE 40

Preparation of 5-Acetyl-2-furancarboxylic acid methyl ester

A solution of 5-formyl-2-furancarboxylic acid methyl ester in 65 ml of tetrahydrofuran was treated with 14 ml of a 3M solution of methyl magnesium bromide in ether at 0°–5° C. The reaction mixture was stirred at the same temperature for 1 hour, poured into a saturated solution of ammonium chloride and extracted with ether. The organic phase was washed with water, dried over anhydrous magnesium sulfate and concentrated giving 6.3 g (87.8%) of 5-(1-hydroxymethyl)-2-furan carboxylic acid methyl ester as a pale yellow oil after chromatographic purification. The oxidation of this secondary alcohol was carried out by using the Swern oxidation conditions. Thus, 6.3 g of 5-(1-hydroxy- methyl) -2-furancarboxylic acid methyl ester in 60 ml of methylene chloride was added to a stirred solution of 5 g of oxalyl chloride, 7.1 g of dimethyl sulfoxide in 80 ml of methylene chloride at −60° C. The reaction mixture was stirred 15 minutes at the same temperature, then 17.5 ml of triethylamine was added. The cooling bath was removed allowing the temperature to rise to 25° C. The reaction mixture was then treated with 25 ml of water, stirred for 10 minutes and extracted with methylene chloride. The organic phase was washed with water, dried over anhydrous magnesium sulfate and concentrated in vacuo to give 6.7 g of a brown oil. Chromatographic purification of this material on a silica gel column followed by crystallization from ethyl acetate-hexane gave 3.5 g (56.2%) of 5-acetyl-2-furancarboxylic acid methyl ester as a white solid, mp 101°–102° C.

Anal. Calcd for $C_8H_8O_4$: C, 57.14; H, 4.80. Found: C, 56.97; H, 4.73.

EXAMPLE 41

Preparation of (E)-5-[1-methyl-2-(1,2,3,4-tetrahydro-9-octyl-9H-dibenzo[b,d]pyrrol-6-yl)-ethenyl]-2-furancarboxylic acid methyl ester Using the conditions described in Example 37, the Wittig condensation reaction of 2.8 g of the phosphonium salt from Example 26 with 0.76 g of 5-acetyl-2-furancarboxylic acid methyl ester from Example 45 produced 1.0 g (52.5%) of (E)-5-[1-methyl-2-(1,2,3,4-tetrahydro-9-octyl-9H-dibenzo[b,d]pyrrol-6-yl)ethenyl]-2-furan carboxylic acid methyl ester as a yellow oil after chromatographic purification.

EXAMPLE 42

Preparation of (E)-5-[1-methyl-2-(1,2,3,4-tetrahydro-1,1-dimethyl-9-octyl-9H-dibenzo[b,d]-pyrrol-6-yl)ethenyl]-2-furancarboxylic acid methyl ester Using the procedure described in Example 37, 3.3 g of the phosphonium salt from Example 27 was condensed with 5-acetyl-2-furancarboxylic acid methyl ester from Example 45 to afford (E)-5-[1-methyl-2-(1,2,3,4-tetrahydro-1,1-dimethyl-9-octyl-9H-dibenzo[b,d]pyrrol-6-yl)ethenyl]-2-furancarboxylic acid methyl ester (1.6 g, 67.7%) as a pale yellow oil after chromatographic purification.

EXAMPLE 43

Preparation of (E)-5-[2-(1,2,3,4-tetrahydro-9-octyl-9H-dibenzo[b,d]pyrrol-6-yl)ethenyl]2-furancarboxylic acid A solution of 6.5 g of (E)-5-[2-(1,2,3,4-tetrahydro-9-octyl-9H-dibenzo [b,d]pyrrol-6-yl)ethenyl]-2-furancarboxylic acid methyl ester from Example 33 in 72 ml of methanol was treated with a solution of 4.9 g of 87% potassium hydroxide in 18 ml of water. The mixture was refluxed for 45 minutes, cooled, diluted with water, acidified with 2N HCl and then extracted with ethyl acetate. The organic phase was washed with water, dried over anhydrous magnesium sulfate and concentrated in vacuo to give 6.0 g of crude acid. Crystallization from ethyl acetate and hexane afforded 4.0 g (63.7%) of (E)-5-[2-(1,2,3,4-tetrahydro-9-octyl-9H-dibenzo[b,d]pyrrol-6-yl)ethenyl]-2-furancarboxylic acid as yellow crystals, mp 142°–144° C.

Anal. Calcd for $C_{27}H_{33}NO_3$: C, 77.29; H, 7.83; N, 3.34. Found: C, 77.26; H, 7.93; N, 3.28.

EXAMPLE 44

Preparation of (E)-5-[2-(1,2,3,4-tetrahydro-1,1-dimethyl-9-octyl-9H-dibenzo[b,d]pyrrol-6-yl)-ethenyl]-2-furancarboxylic acid Using the procedure of Example 48, 5.5 g of the methyl ester from Example 34 was saponified giving (E)-5-[2-(1,2,3,4-tetrahydro-1,1-dimethyl -9-octyl-9H-dibenzo[b,d]pyrrol-6-yl)ethenyl]-2-furancarboxylic acid (3.0 g; 56%) as yellow crystals after crystallization from ethyl acetate-hexane, mp 135°–137.5° C.

Anal. Calcd for $C_{29}H_{37}NO_3$: C, 77.82; H, 8.33; N, 3.13. Found: C, 77.98; H, 8.36; N, 3.13.

EXAMPLE 45

Preparation of (E)-5-[2-(1,2,3,4-tetrahydro-3,3-dimethyl-9-octyl9H-dibenzo[b,d]pyrrol-6-yl)-ethenyl]-2-furancarboxylic acid Using the procedure of Example 43, 2.1 g of methyl ester from Example 35 was saponified to give 1.2 g.(59%) of (E)-5-[2-(1,2,3,4-tetrahydro-3,3dimethyl-9-octyl-9 H-dibenzo[b,d]-pyrrol-6yl)ethenyl]-2-furancarboxylic acid as a yellow solid after crystallization from ethyl acetate-hexane, mp 150°–153° C.

Anal. Calcd for $C_{29}H_{37}NO_3$: C, 77.82; H, 8.33; N, 3.13. Found: C, 7.73; H, 8.48; N, 3.12.

EXAMPLE 46

Preparation of (E)-5-[2-(1,2,3,4-tetrahydro-2,2,4,4-tetramethyl-9-octyl-9H-dibenzo[b,d]pyrrol-6-yl)ethenyl]-2-furancarboxylic acid Using the procedure of Example 43, 0.8 g of the methyl ester from Example 36 was saponified to (E)-5-[2-(1,2,3,4-tetrahydro-2,2,4,4-tetramethyl-9-octyl-9H-dibenzo[b,d]pyrrol-6-yl)ethenyl]-2-furancarboxylic acid in 39% yield as yellow crystals after crystallization from ethyl acetate-hexane, mp 155.5°–157.5° C.

Anal. Calcd for $C_{31}H_{41}NO_3$: C,78.28; H, 8.69; N, 2.94. Found: C, 78.32; H, 9.00; N, 3.02.

EXAMPLE 47

Preparation of (E)-5-[2-methyl-2-(1,2,3,4-tetrahydro-9-octyl-9H-dibenzo[b,d]pyrrol-6-yl)-ethenyl]-2-furancarboxylic acid Using the procedure of Example 43, 1.46 g of the methyl ester from Example 37 was saponified and purified by crystallization from ethyl acetate-hexane to give (E)-5-[2-methyl-2-(1,2,3,4-tetrahydro-9-octyl-9H-dibenzo[b,d]pyrrol-6-yl)ethenyl]-2-furancarboxylic acid in 47.2% yield as yellow crystals, mp 151.5°–153.5° C.

Anal. Calcd for $C_{28}H_{35}NO_3$: C, 77.56; H, 8.14; N, 3.23. Found: C, 77.65; H, 8.30; N, 3.22.

EXAMPLE 48

Preparation of (E)-5-[2-methyl-2-(1,2,3,4-tetrahydro-1,1-dimethyl-9-octyl -9H-dibenzo[b,d]-pyrrol-6yl)ethenyl]-2-furancarboxylic acid Using the procedure of Example 43, 0.7 g of the ester from Example 38 was saponified to (E)-5-[2-methyl-2-(1,2,3,4-tetrahydro1,1 -dimethyl-9-octyl-9H-dibenzo[b,d]-pyrrol-6-yl)ethenyl]-2-furancarboxylic acid in 39% yield as a pale yellow solid after crystallization from ethyl acetate-hexane, mp-147°–149° C.

Anal. Calcd for $C_{30}H_{39}NO_3$: C, 78.05; H, 8.52; N, 3.03. Found: C, 78.01; H, 8.53; N, 2.96.

EXAMPLE 49

Preparation of (E)-5-[2-methyl-2-(1,2,3,4-tetrahydro-2,2,4,4-tetramethyl-9-octyl-9H-dibenzo-[b,d]pyrrol-6-yl)ethenyl]-2-furancarboxylic acid Using the procedure of Example 43, 0.56 g of the methyl ester from Example 39 was saponified to (E)-5-[2-methyl-2-(1,2,3,4-tetrahydro-2,2,4,4-tetramethyl-9-octyl-9H-dibenzo[b,d]pyrrol-6yl)ethenyl]-2-furancarboxylic acid (0.133 g, 24.2%) as a yellow solid after crystallization from ethyl acetate-hexane, mp. 140°–142.5° C.

Anal. Calcd for $C_{32}H_{43}NO_3$: C, 78.49; H, 8.85; N, 2.86. Found: C, 78.53; H, 8.79; N, 2.80.

EXAMPLE 50

Preparation of (E)-5-[1-methyl-2-(1,2,3,4-tetrahydro-]-octyl-9H-dibenzo[b,d]pyrrol-6-yl)ethenyl]-2-furancarboxylic acid Using the procedure of Example 43, 0.756 g of the methyl ester from Example 41 was saponified and purified by crystallization from ethyl acetate to give (E)-5-[1-methyl-2-(1,2,3,4-tetrahydro-9-octyl-9H-dibenzo[b,d]-pyrrol-6-yl)ethenyl]-2-furancarboxylic acid (0.334 g; 45.6%) as yellow crystals, mp 160.0°–162.5° C.

Anal. Calcd for $C_{28}H_{35}NO_3$: C, 77.56; H, 8.14; N, 3.23. Found: C, 77.30; H, 8.27; N, 3.18.

EXAMPLE 51

Preparation of (Z)-5-[2-(1,2,3,4-tetrahydro-9-octyl-9H-dibenzo[b,d]pyrrol-6-yl)ethenyl]-2-furancarboxylic acid Using the procedure of Example 43, the hydrolysis of 1.7 g of the methyl ester obtained from chromatographic fractions enriched in the (Z) isomer from Example 33 gave (Z)-5-[2-(1,2,3,4-tetrahydro-9-octyl-9H-dibenzo[b,d]pyrrol-6-yl)ethenyl]-2-furancarboxylic acid (1.1 g; 67.2%) as pale yellow crystals after crystallization from ethyl acetate-hexane, mp 128°–131° C.

Anal. Calcd for $C_{27}H_{33}NO_3$: C, 77.29; H, 7.93; N, 3.34. Found: C, 77.15; H, 7.97; N, 3.26.

EXAMPLE 52

Preparation of (Z)-5-[2-(1,2,3,4-tetrahydro-1,1-dimethyl-9-octyl-9H-dibenzo[b,d]pyrrol-6-yl)-ethenyl]2-furancarboxylic acid Using the procedure described in Example 43, 3.8 g of the methyl ester from Example 34 (minor component) was saponified to (Z)-5-[2-(1,2,3,4-tetrahydro-1,1-dimethyl-9-octyl-9H-dibenzo[b,d]-pyrrol-6-yl)ethenyl]-2-furancarboxylic acid (1.67 g, 45.5%) as a pale yellow solid after crystallization from ethyl acetate-hexane, mp. 115°–117° C.

Anal. Calcd for $C_{29}H_{37}NO_3$: C, 77.82; H, 8.33; N, 3.13. Found: C, 78.12; H, 8.45; N, 3.06.

EXAMPLE 53

Preparation of (E)-5-[1-methyl-2-( 1,2,3,4-tetrahydro-1,1dimethyl-9-octyl -9H-dibenzo[b,d]-pyrrol-6-yl)ethenyl]-2-furancarboxylic acid Using the procedure of Example 43, 1.6 g of the methyl ester from Example 42 was saponified to (E)-5-[1-methyl-2-(1,2,3,4-tetrahydro-1,1-dimethyl-9-octyl-9H-dibenzo[b,d]pyrrol-6-yl)ethenyl]-2-furancarboxylic acid (0.78 g; 50%) as a pale yellow solid after crystallization from ethyl acetate-hexane, mp-135°–137° C.

Anal. Calcd for $C_{30}H_{39}NO_3$: C, 78.05; H, 8.52; N, 3.03. Found: C, 77.89; H, 8.48; N, 3.22.

EXAMPLE 54

Preparation of 5-[2-(1,2,3,4-tetrahydro-9-octyl-9H-dibenzo[b,d]pyrrol-6yl)ethyl]-2-furancarboxylic acid methyl ester The hydrogenation of (E)-5-[2-(1,2,3,4-tetrahydro-9-octyl-9H-dibenzo[b,d]pyrrol-6-yl)ethenyl]-2-furancarboxylic acid methyl ester from Example 33 was carried out at normal pressure and at room temperature. Thus 5.3 g of this material dissolved in 55 ml of absolute ethyl alcohol was hydrogenated in the presence of 0.3 g of 10% Palladium on carbon to give 4.0 g (76.0%) of 5-[2-(1,2,3,4tetrahydro-9-octyl-9H-dibenzo[b,d]pyrrol-6yl)ethyl]-2-furancarboxylic acid methyl ester as a yellow oil after chromatographic purification.

EXAMPLE 55

Preparation of 5-[2-(1,2,3,4-tetrahydro-9-octyl-9H-dibenzo[b,d]pyrrol-6yl) ethyl]-2-furancarboxylic acid Using the procedure described in Example 43, 3.9 g of the methyl ester from Example 54 was saponified to 5-[2-(1,2,3,4-tetrahydro-9-octyl -9H-dibenzo[b,d]pyrrol-6-yl)ethyl]-2-furancarboxylic acid (1.2 g) in 31.8% yield as a white solid, after repeated crystallizations from ethyl acetate-hexane, mp 109.5°–111.0° C.

Anal. calcd for $C_{27}H_{35}NO_3$: C, 76.96; H, 8.31; N, 3.37. Found: C, 77.12; H, 8.44; N, 3.17.

EXAMPLE 56

Preparation of 1,2,3,4,tetrahydro-6-phenylmethoxy-9H-dibenzo[b,d]pyrrole

Using the procedure of Example 1, the reaction of 98.0 g of 4-benzyloxyphenylhydrazine hydrochloride with 31.6 g of cyclohexanone in 790 mL of 80% aqueous acetic acid produced 42.1g(38.8%) of 1,2,3,4-tetrahydro-6-phenylmethoxy-9H-dibenzo[b,d]pyrrole as a brown solid after crystallization from hexane-ethyl acetate.

EXAMPLE 57

Preparation of 1,2,3,4-tetrahydro-7-phenylmethoxy-9H-dibenzo[b,d]pyrrole

Using the procedure of Example 1, 17.2 g of 3-benzyloxyphenyl hydrazine hydrochloride was reacted with 6.8 g of cyclohexanone in 80% aqueous acetic acid giving 6.9 g (36.3%) of 1,2,3,4-tetrahydro-7-phenylmethoxy-9H-dibenzo[b,d]pyrrole as a tan solid. This material was used without purification.

EXAMPLE 58

Preparation of 1,2,3,4-tetrahydro-1,1-dimethyl-6-phenylmethoxy-9H-dibenzo[b,d]pyrrole Using the procedure of Example 1, 10.0 g of 4-benzyloxyphenylhydrazine hydrochloride was reacted with 5.1 g of 2,2-dimethylcyclohexanone in 100 mL of 80% aqueous acetic acid to give 7.7 g (63.5%) of 1,2,3,4-tetrahydro-1,1-dimethyl-6-phenylmethoxy-9H-dibenzo[b,d]pyrrole as a pale yellow solid after chromatographic purification.

EXAMPLE 59

Preparation of 1,2,3,4-tetrahydro-3,3-dimethyl-6-phenylmethoxy-9H-dibenzo[b,d]pyrrole Using the procedure of Example 1,4.5 g of 4-benzyloxyphenylhydrazine hydrochloride was reacted with 8.9 g of 4,4-dimethylcyclohexanone in 100 ml of 80% aqueous acetic acid to give 4.3 g (90.2%) of 1,2,3,4-tetrahydro-3,3-dimethyl-6-phenylmethoxy-9H-dibenzo[b,d]pyrrole as a tan solid after purification with activated carbon (Darco G-60) and repeated crystallizations.

EXAMPLE 60

Preparation of rac- 1,2,3,4-tetrahydro-1-(3-methoxyphenyl)-6-phenylmethoxy -9H-dibenzo[b,d]pyrrole Using the procedure described in Example 1, 4.5 g of 4-benzyloxy phenylhydrazine hydrochloride was condensed with 3.7 g of 2-(3-methoxyphenyl)cyclohexanone in 80% aqueous acetic acid to give 3.0 g (43.8.0%) of 1,2,3,4-tetrahydro-1(3-methoxyphenyl)-6-phenylmethoxy -9H-dibenzo[b,d]pyrrole as a yellow oil.

EXAMPLE 61

Preparation of 2-octylcyclohexanone

A 4.0 g portion of 60% sodium hydride-mineral oil dispersion was washed with hexane and suspended in 150 ml of anhydrous DMF. To the stirred slurry was slowly added a solution of 17.0 g of ethyl cyclohexanone-2-carboxylate in 50 ml of anhydrous DMF at room temperature. After being stirred at room temperature for 45 minutes, the gas evolution ceased. The mixture was treated with a solution of 38.0 g of 1-iodooctane in 50 ml of anhydrous DMF and stirred at room temperature overnight. The mixture was poured into water and worked up with ether giving 42.8 g of a yellow viscous oil. Purification of this material on a chromatographic column of silica gel (eluting system: ether-hexane 1:1) yielded 24.0 g (95.8%) of 1-octylcyclohexan-2-one-1-carboxylic acid ethyl ester A portion of 18.0 g of this material dissolved in 60 ml of anhydrous DMSO was treated with 5.6 g of lithium chloride and gently refluxed for 5 hours. The mixture was poured into water and extracted with ether. The organic phase was washed with water, dried over anhydrous magnesium sulfate and concentrated to give 11.1 g (83%) of 2-octylcyclohexanone as a pale yellow oil after chromatographic purification on a silica gel column (eluting system: hexane-ether 4:1).

EXAMPLE 62

Preparation of rac-1,2,3,4-tetrahydro-1-octyl-6-phenylmethoxy-9H-dibenzo[b,d]pyrrole Using the procedure of Example 1, 3.0 g of 4-benzyloxyphenylhydrazine hydrochloride was reacted with 2-octylcyclohexanone from Example 61 in 80% aqueous acetic acid to produce 2.9 g (62.5%) of 1,2,3,4-tetrahydro-1-octyl-6-phenylmethoxy-9H-dibenzo[b,d]pyrrole as a pale yellow solid after chromatographic purification.

EXAMPLE 63

Preparation of 1,2,3,4-tetrahydro-6-phenylmethoxy-9-octyl-9H-dibenzo[b,d]pyrrole Using the procedure of Example 9, 37.4 g of 1,2,3,4-tetrahydro-6-phenylmethoxy-9H-dibenzo[b,d]pyrrole from Example 56 was alkylated with 1-bromooctane (27.9 g; 0.145 mol) giving 45.6 g (86.8%) of 1,2,3,4-tetrahydro-6-phenylmethoxy-9-octyl-9H-dibenzo-[b,d]pyrrole as a yellow oil after chromatographic purification.

EXAMPLE 64

Preparation of 1,2,3,4-tetrahydro-7-phenylmethoxy-9-octyl-9H-dibenzo[b,d]pyrrole Using the procedure of Example 9, 6.9 g of 1,2,3,4-tetrahydro-7-phenylmethoxy -9H-dibenzo[b,d]pyrrole from Example 57 was alkylated with 1-bromooctane (5.25 g) giving 9.0 g (92.8%) of 1,2,3,4-tetrahydro-7-phenylmethoxy-9-octyl-9H-dibenzo[b,d]pyrrole as a yellow oil after chromatographic purification.

EXAMPLE 65

Preparation of 1,2,3,4-tetrahydro-1,1-dimethyl-6-phenylmethoxy-9-octyl -9H-dibenzo[b,d]-pyrrole Using the procedure of Example 9, the alkylation of 7.7 g of 1,2,3,4-tetrahydro-1,1-dimethyl-6-phenylmethoxy-9H-dibenzo[b,d]pyrrole from Example 58 was reacted with 5.48 g of 1-bromooctane to produce 5.3 g (50.5%) of 1,2,3,4-tetrahydro-1,1-dimethyl-6-phenylmethoxy-9-octyl-9H-dibenzo-[b,d]pyrrole as an orange oil after chromatographic purification.

EXAMPLE 66

Preparation 1,2,3,4-tetrahydro-3,3-dimethyl-6-phenylmethoxy-9-octyl-9H-dibenzo[b,d]pyrrole Using the procedure of Example 9, the alkylation of 4.3 g of 1,2,3,4-tetrahydro-3,3-dimethyl-6-phenylmethoxy-9H-dibenzo[b,d]pyrrole from Example 59 was reacted with 2.92 g of 1-bromooctane to produce 5.5 g (94%) of 1,2,3,4-tetrahydro-3,3-dimethyl-6-phenylmethoxy -9-octyl-9H-dibenzo[b,d]pyrrole as a white solid after chromatographic purification.

EXAMPLE 67

Preparation of 1,2,3,4-tetrahydro-6-phenylmethoxy-9-butyl-9H-dibenzo[b,d]pyrrole Using the procedure of Example 9, the alkylation of 5.0 g. of 1,2,3,4-tetrahydro-6-phenylmethoxy-9H-dibenzo[b,d]pyrrole from Example 56 was reacted with 1-bromobutane (2.68 g) to give 5.3 g (88.2%) of 1,2,3,4-tetrahydro-6-phenylmethoxy-9-butyl-9H-dibenzo[b,d]pyrrole as a yellow oil after chromatographic purification.

EXAMPLE 68

Preparation 1,2,3,4-tetrahydro-6-phenylmethoxy-9-(4-bromophenyl) methyl-9H-dibenzo[b,d]pyrrole Using the procedure of Example 9, the alkylation of 5.0 g of 1,2,3,4-tetrahydro-6-phenylmethoxy-9H-dibenzo[b,d]pyrrole from Example 56 with 4-bromobenzyl bromide (5.0 g) afforded 1,2,3,4-tetrahydro-6-phenylmethoxy-9-(4-bromophenyl)methyl-9H-dibenzo[b,d]pyrrole (5.0 g; 62.1%) as a pale yellow solid after chromatographic purification.

EXAMPLE 69

Preparation of 1,2,3,4-tetrahydro-6-phenylmethoxy-9-methyl-9H-dibenzo[b,d]pyrrol Using the procedure of Example 9, the alkylation of 7.0 g. of 1,2,3,4-tetrahydro-6-phenylmethoxy-9H-dibenzo[b,d]pyrrole from Example 56 with methyl iodide gave 5.6 g (76.2%) of 1,2,3,4-tetrahydro-6-phenylmethoxy-9-methyl-9H-dibenzo[b,d]pyrrole as a yellow solid after chromatographic purification.

EXAMPLE 70

Preparation of 1,2,3,4-tetrahydro-6-phenylmethoxy-9-(4-chlorophenyl)methyl-9H-dibenzo[b,d]pyrrole Using the procedure of Example 9, the alkylation of 7.0 g of 1,2,3,4-tetrahydro-6-phenylmethoxy-9H-dibenzo[b,d]pyrrole from Example 56 with 4-chlorobenzyl chloride (4.4 g) produced 8.0 g (78.8%) of 1,2,3,4-tetrahydro-6-phenylmethoxy-9-(4-chlorophenyl)methyl-9H-dibenzo[b,d]pyrrole as a yellow oil after chromatographic purification.

EXAMPLE 71

Preparation of 1,2,3,4-tetrahydro-6-phenylmethoxy-9-heptyl-9H-dibenzo[b,d]pyrrole Using the procedure of Example 9, the alkylation of 5.5 g of 1,2,3,4-tetrahydro-6-phenylmethoxy-9H-dibenzo[b,d]pyrrole from Example 56 with 1-bromoheptane (3.77 g) gave 6.4 g (86.0%) of 1,2,3,4-tetrahydro-6-phenylmethoxy-9-heptyl-9 H-dibenzo[b,d]pyrrole as a yellow oil after chromatographic purification.

EXAMPLE 72

Preparation of 1,2,3,4-tetrahydro-6phenylmethoxy-9-nonyl-9H-dibenzo[b,d]pyrrole.

Using the procedure of Example 9, the alkylation of 5.5 g of 1,2,3,4-tetrahydro-6-phenylmethoxy-9H-dibenzo[b,d]pyrrole from Example 56 with 1-bromononane (4.33 g) gave 1,2,3,4-tetrahydro-6-phenyl-methoxy -9-nonyl-9H-dibenzo[b,d]pyrrole (6.9 g) as a yellow oil after chromatographic purification.

EXAMPLE 73

Preparation of 1,2,3,4-tetrahydro-6-phenylmethoxy-9-dodecyl-9H-dibenzo[b,d]pyrrole Using the procedure of Example 9, the alkylation of 5.5 g of 1,2,3,4-tetrahydro-6-phenylmethoxy-9H-dibenzo[b,d]pyrrole from Example 56 with 1-bromododecane (5.19 g) afforded 6.8 g (77.2%) of 1,2,3,4-tetrahydro-6-phenylmethoxy-9-dodecyl-9H-dibenzo[b,d]pyrrole as a yellow oil after chromatographic purification.

EXAMPLE 74

Preparation of 9-(4-heptylphenyl)methyl-6-phenylmethoxy-1,2,3,4-tetrahydro-9H-dibenzo[b,d]pyrrole Using the procedure of Example 9, the akylation of 1,2,3,4-tetrahydro-6-phenylmethoxy-9H-dibenzo[b,d]pyrrole (5.5 g) from Example 56 with 4-heptylbenzyl bromide (5.6 g) afforded 6.2 g (67.4%) of 1,2,3,4-tetrahydro-6-phenylmethoxy-9-(4-heptylphenyl)-methyl-9H-dibenzo[b,d]pyrrole as a yellow oil after chromatographic purification.

EXAMPLE 75

Preparation (E)-9-(3,7-dimethyl-2,6-octadienyl)-1,2,3,4-tetrahydro-(6-phenylmethoxy)-9H-dibenzo[b,d]pyrrole Using the procedure of Example 9, the alkyation of 1,2,3,4-tetrahydro-6-phenylmethoxy-9H-dibenzo[b,d]pyrrole (4.1 g) from Example 56 with geranyl bromide (3.27 g) afforded 4.0 g (65.7%) of 1,2,3,4-tetrahydro-6-phenylmethoxy-9-[(3,7-dimethyl )-2,6-dieneoctyl]-9H-dibenzo[b,d]pyrrole as a yellow oil after chromatographic purification.

EXAMPLE 76

Preparation of 9-(4-phenylbutyl)-6-phenylmethoxy-1,2,3,4-tetrahydro-9H-dibenzo[b,d]pyrrole Using the procedure of Example 9, the alkylation of 1,2,3,4-tetrahydro-6-phenylmethoxy-9H-dibenzo[b,d]pyrrole (4.5 g) from Example 56 with benzenebutanol methanesulfonate (3.8 g) produced 6.0 g (90.3%) of 1,2,3,4-tetrahydro-6-phenylmethoxy-9-(4-phenylbutyl)-9H-dibenzo[b,d]pyrrole as a yellow oil after chromatographic purification.

EXAMPLE 77

Preparation of 1,2,3,4-tetrahydro-6-phenylmethoxy-9-[(4-fluorophenyl) methyl]-9H-dibenzo[b,d]pyrrole A solution of 1,2,3,4-tetrahydro-6-(phenylmethoxy)-9H-dibenzo[b,d]pyrrole (2.77 g) in dimethylformamide (20 mL) was stirred under argon at room temperature and treated with a 55% oil dispersion of sodium hydride in mineral oil (0.48 g). After stirring for ten minutes, a solution of 4-fluorobenzyl chloride (1.73 g) in dimethylformamide (5 mL) was added and the mixture was stirred for an additional 30 minutes. The solvent was removed by evaporation and the residue was mixed with water and extracted with dichloromethane. The organic phase was dried over sodium sulfate, concentrated and the residue was purified by HPLC chromatography (eluting system: dichloromethane-hexane 1:2) and crystallization from ether-hexane to produce 2.9 g (75%) of 1,2,3,4-tetrahydro-6-(phenylmethoxy)-9-[(4-fluorophenyl)methyl]-9H-dibenzo[b,d]pyrrole, mp 134°–135° C.

EXAMPLE 78

Preparation of 1,2,3,4-tetrahydro-6-(phenylmethoxy)-9-[(3-Fluorophenyl) methyl]-9H-dibenzo[b,d]pyrrole Using the procedure of Example 77, the alkylation of 1,2,3,4-tetahydro-6-(phenylmethoxy)-9H-dibenzo[b,d]pyrrole (2.77 g) from Example 56 with 3-fluorobenzyl bromide (2.27 g) provided 2.9 g (75%) of 9-[(3-fluorophenyl)methyl]-1,2,3,4-tetrahydro-6-(phenylmethoxy)-9H-dibenzo[b,d]pyrrole after HPLC chromatography using dichloromethane-hexane (1:2) as eluent and crystallization from ether-hexane, mp 97°–98° C.

EXAMPLE 79

Preparation of 1,2,3,4-tetrahydro-6-(phenylmethoxy)-9-[(2-Fluorophenyl)methyl]-9H-dibenzo[b,d]pyrrole Using the procedure of Example 77, the alkylation of 1,2,3,4-tetrahydro-6-(phenylmethoxy)-9H-dibenzo[b,d]pyrrole (2.77 g) from Example 56 with 2-fluorobenzyl bromide (2.27 g) provided 2.8 g (73%) of 9-[(2-fluorophenyl) methyl]-1,2,3,4-tetrahydro-6-(phenylmethoxy) -9H-dibenzo[b,d]pyrrole after HPLC chromatography (eluting system: dichloromethane-hexane 1:2) and crystallization from ether-hexane, mp 105°–106° C.

EXAMPLE 80

Preparation of 1,2,3,4-tetrahydro-9-[(4-methoxyphenyl)methyl]-6-(phenylmethoxy) -9H-dibenzo[b,d]pyrrole Using the procedure of Example 77, the alkylation of 1,2,3,4-tetahydro-6-(phenylmethoxy)-9H-dibenzo[b,d]pyrrole (2.77 g) from Example 56 with 4-methoxybenzyl chloride (1.88 g) gave 2.2 g (55%) of 1,2,3,4-tetrahydro-9-[(4-methoxyphenyl)methyl]-6-(phenyl,methoxy) -9H-dibenzo[b,d]pyrrole after HPLC chromatography using dichloromethane-hexane (1:1) as eluent and crystallization from ether-hexane mp 99°–100° C.

EXAMPLE 81

Preparation of 1,2,3,4-tetrahydro-6-(phenylmethoxy)-9-(3,4dimethoxyphenyl)methyl]-9H-dibenzo[b,d]pyrrole Using the procedure of Example 77, the alkylation of 1,2,3,4-tetrahydro-6-(phenylmethoxy)-9H-dibenzo[b,d]pyrrole (2.77 g) from Example 56 with 3,4-dimethoxybenzyl chloride (2.24 g) produced 2.5 g (58%) of 1,2,3,4-tetrahydro-6-(phenylmethoxy)-9-[(3,4dimethoxyphenyl)methyl]-9H-dibenzo[b,d]pyrrole, after HPLC chromatography using dichloromethane-hexane (1:2) and crystallization from ether-hexane, mp 99°–100° C.

EXAMPLE 82

Preparation of 1,2,3,4-tetrahydro-9-[(4-methylphenyl)-methyl]-6-(phenylmethoxy)-9H-dibenzo[b,d]pyrrole Using the procedure of Example 77, the alkylation of 1,2,3,4-tetrahydro-6-(phenylmethoxy)-9H-dibenzo[b,d]pyrrole (2.77 g) from Example 56 with alpha-bromo-p-xylene (2.22 g) provided 2.3 g (60%) of 1,2,3,4-tetrahydro-9-[(4-methylphenyl)methyl]-6-(phenylmethoxy methoxy)-9H-dibenzo[b,d]pyrrole after HPLC chromatography using dichloromethane-hexane (1:3) and crystallization from dichloromethane-hexane, mp 122°–123° C.

EXAMPLE 83

Preparation of 1,2,3,4-tetrahydro-9-[(2,4,6-trimethylphenyl) methyl]-6-(phenylmethoxy)-9H-dibenzo[b,d]pyrrole Using the procedure of Example 77, the alkylation of 1,2,3,4-tetrahydro-6-(phenylmethoxy)-9H-dibenzo[b,d]pyrrole (2.77 g) from Example 56 with alpha$^2$-chloroisodurene (2.02 g) provided 3.7 g (96%) of 1,2,3,4-tetrahydro-9-[(2,4,6-trimethylphenyl)methyl]-6-

(phenylmethoxy)-9H-dibenzo[b,d]pyrrole after crystallization from dichloromethane-hexane, mp 169°–170° C.

EXAMPLE 84

Preparation of rac-1,2,3,4-tetrahydro-1-(3-methoxyphenyl)-6-phenylmethoxy -9-octyl-9 H-dibenzo[b,d]pyrrole Using the procedure of Example 9, 3.0 g of 1,2,3,4tetrahydro-1-(3-methoxyphenyl)-6-phenylmethoxy-9H-dibenzo[b,d]pyrrole from Example 60 was alkylated with 1.79 g of 1-bromooctane to provide 3,4 g (88.0%) of rac-1,2,3,4-tetrahydro-1-(3-methoxyphenyl) -6-phenylmethoxy-9H-dibenzo[b,d]pyrrole as a pale yellow oil after chromatographic purification.

EXAMPLE 85

Preparation of rac-1,2,3,4-tetrahydro-1,9-dioctyl-6-phenylmethoxy-9H-dibenzo[b,d]pyrrole Using the procedure of Example 9, 2.9 g of 1,2,3,4-tetrahydro-1-octyl-6-phenylmethoxy-9H-dibenzo[b,d]pyrrole from Example 62 was alkylated with 1.68 g of 1-bromooctane to produce 2.3 g (61.7%) of rac-1,2,3,4-tetrahydro-1,9-dioctyl-6-phenylmethoxy-9H-dibenzo[b,d]pyrrole as a yellow oil after chromatographic purification.

EXAMPLE 86

Preparation of 5,6,7,8-tetrahydro-9-octyl-9H-dibenzo[b,d]pyrrol-3-ol

The hydrogenation of 1,2,3,4-tetrahydro-6-phenylmethoxy-9-octyl-9H-dibenzo[b,d]pyrrole from Example 63 was carried out at atmospheric pressure and at room temperature. Thus, 12.5 g of this material dissolved in 125 mL of absolute ethanol and 75 mL of ethyl acetate was hydrogenated in the presence of 0.6 g of 10% Palladium on carbon. The mixture was filtered on celite, the solvents evaporated in vacuo and the residue was chromatographed on silica gel to give 9.5 g (98.5%) of 1,2,3,4-tetrahydro-9-octyl-9H-dibenzo[b,d]pyrrol-3-ol as a yellow oil.

EXAMPLE 87

Preparation of -5,6,7,8-tetrahydro-9-octyl-9H-dibenzo[b,d]pyrrol-2-ol

Using the procedure of Example 86, 9.0 g of the benzyloxy derivative from Example 64 was hydrogenated giving 7.8 g (100%) of 5,6,7,8-tetrahydro-9-octyl-9H-dibenzo[b,d]pyrrol-2-ol as a yellow oil.

EXAMPLE 88

Preparation of 5,6,7,8,tetrahydro-8,8-dimethyl-9-octyl-9H-dibenzo[b,d]pyrrol-3-ol Using the procedure of Example 86, 5.3 g of the benzyloxy derivative from Example 65 was hydrogenated giving 4.0 g (96.5%) of 5,6,7,8-tetrahydro-8,8-dimethyl-9-octyl-9H-dibenzo[b,d]pyrrol-3-ol as a pink oil.

EXAMPLE 89

Preparation of 5,6,7,8-tetrahydro-6,6-dimethyl-9-octyl-9H-dibenzo[b,d]pyrrole-3-ol Using the procedure of Example 86, 5.5 g of the benzyloxy derivative from Example 66 was hydrogenated giving 5.0 g of 5,6,7,8-tetrahydro-6,6-dimethyl-9-octyl-9H-dibenzo[b,d]pyrrol-3-ol as a viscous yellow oil after chromatographic purification.

EXAMPLE 90

Preparation of 5,6,7,8-tetrahydro-9-butyl-9H-dibenzo[b,d]pyrrol-3-ol

Using the procedure of Example 86, 5.3 g of the benzyloxy derivative from Example 67 was hydrogenated giving 3.8 g (98.2%) of 5,6,7,8-tetrahydro-9-butyl-9H-dibenzo[b,d]pyrrol-3-ol as a yellow oil.

EXAMPLE 91

Preparation of 5,6,7,8-tetrahydro-9-(4-bromophenyl)-methyl)-9H-dibenzo[b,d]pyrrole-3-ol Using the procedure of Example 86, 5.0 g of the benzyloxy derivative from Example 68 was hydrogenated giving 2.4 g (60.1%) of 5,6,7,8-tetrahydro-9-(4-bromophenyl)-methyl-9H-dibenzo[b,d]pyrrol-3-ol as a yellow oil.

EXAMPLE 92

Preparation of 5,6,7,8-tetrahydro-9-methyl-9H-dibenzo[b,d]pyrrol-3-ol

Using the procedure of Example 86, 5.6 g of the benzyloxy derivative from Example 69 was hydrogenated giving 3,4 g (87.8%) of 5,6,7,8-tetrahydro-9-methyl-9H-dibenzo[b,d]pyrrol-3-ol as a yellow oil.

EXAMPLE 93

Preparation of 5,6,7,8-tetrahydro-9-(4-chlorophenyl)-methyl-9H-dibenzo[b,d]pyrrol-3-ol Using the procedure of Example 86, 8.0 g of the benzyloxy derivative from Example 70 was hydrogenated giving 5.6 g (90.3%) of 5,6,7,8-tetrahydro-9-(4-chlorophenyl)methyl-9H-dibenzo [b,d]pyrrol-3-ol as a pale yellow solid. This material was used without further purification.

EXAMPLE 94

Preparation of 5,6,7,8-tetrahydro-9-heptyl-9H-dibenzo[b,d]pyrrol-3-ol

Using the procedure of Example 86, 6.4 g of the benzyloxy derivative from Example 71 was hydrogenated giving 4.9 g (100%) of 5,6,7,8-tetrahydro-9-heptyl-9H-dibenzo[b,d]pyrrol-3-ol as a yellow oil.

EXAMPLE 95

Preparation of 5,6,7,8-tetrahydro-9-nonyl-9H-dibenzo[b,d]pyrrol-3-ol

Using the procedure of Example 86, 6.9 g of the benzyloxy derivative from Example 72 was hydrogenated giving 4.7 g (87.8%) of 5,6,7,8-tetrahydro-9-nonyl-9H-dibenzo[b,d]pyrrol-3-ol as a yellow oil.

EXAMPLE 96

Preparation of 5,6,7,8-tetrahydro-9-dodecyl-9H-dibenzo[b,d]pyrrol-3-ol

Using the procedure of Example 86, 6.8 g of the benzyloxy derivative from Example 73 was hydrogenated giving 5.2 g (95.4%) of 5,6,7,8-tetrahydro-9-dodecyl-9H-dibenzo[b,d]pyrrol-3-ol as a dark yellow oil.

EXAMPLE 97

Preparation of 5,6,7,8-tetrahydro-9-(4-heptylphenyl)-methyl-9H-dibenzo[b,d]pyrrol-3-ol Using the procedure of Example 86, 6.2 g. of the benzyloxy derivative from Example 74 was hydrogenated giving 3.7 g (74%) of 5,6,7,8-tetrahydro-9-(4-heptylphenyl)methyl-9H-dibenzo[b,d]pyrrol-3-ol as a yellow oil.

EXAMPLE 98

Preparation of 5,6,7,8-tetrahydro-9-[(3,7-dimethyl)octyl]-9H-dibenzo[b,d]pyrrol-3-ol Using the procedure of Example 86, 12.2 g of the benzyloxy derivative from Example 75 was hydrogenated providing 10.4 g in almost quantitative yield of 5,6,7,8-tetrahydro-9-[(3,7-dimethyl)octyl]-9H-dibenzo[b,d]pyrrol-3-ol as a yellow oil after chromatographic purification.

EXAMPLE 99

Preparation of 5,6,7,8-tetrahydro-9-(4-phenylbutyl)-9H-dibenzo[b,d]pyrrol-3-ol

Using the procedure of Example 86, the hydrogenation of 1,2,3,4-tetrahydro-6-phenylmethoxy-9-(4-phenylbutyl)-9 H-dibenzo[b,d]pyrrole (6.0 g) from Example 76 gave 4.2 g (90%) of 5,6,7,8-tetrahydro-9-(4-phenylbutyl)-9H-dibenzo[b,d]pyrrol-3-ol as a yellow oil after chromatographic purification.

EXAMPLE 100

Preparation of 5,6,7,8-tetrahydro-9-[(4-fluorophenyl)methyl]-9H-dibenzo[b,d]pyrrol-3-ol The hydrogenation of 2.8 g of 1,2,3,4-tetrahydro-6-phenylmethoxy -9-[(4-fluorophenyl)methyl]-9H-dibenzo[b,d]pyrrole from Example 77 was carried out by using the procedure described in Example 86 except that 1:1 tetrahydrofuran-absolute ethyl alcohol was used instead of 1:1 ethyl acetate-absolute ethyl alcohol mixture as a solvent. The crude 5,6,7,8-tetrahydro-9-[(3-fluorophenyl)methyl]-9H-dibenzo[b,d]pyrrol-3-ol was used without further purification.

EXAMPLE 101

Preparation of 5,6,7,8-tetrahydro-9-[(3-fluorophenyl)methyl]-9H-dibenzo[b,d]pyrrol-3-ol Using the procedure of Example 100, the hydrogenation of 2.8 g of 1,2,3,4-tetrahydro-6-phenylmethoxy-9-[(3-fluorophen yl)methyl]-9H-dibenzo[b,d]pyrrole from Example 78 provide crude 5,6,7,8-tetrahydro-9-[(3-fluorophenyl)methyl]-9H-dibenzo[b,d]pyrrol-3-ol which was used without further purification.

EXAMPLE 102

Preparation of 5,6,7,8-tetrahydro-9-[(2-fluorophenyl)methyl]-9H-dibenzo[b,d]pyrrol-3-ol Using the procedure of Example 100, the hydrogenation of 2.7 g of 1,2,3,4-tetrahydro-6-phenylmethoxy-9-[(2-fluorophenyl)methyl]-9H-dibenzo[b,d]pyrrole from Example 79 gave 5,6,7,8-tetrahydro-9-[(2fluorophenyl)methyl]-9H-dibenzo[b,d]pyrrol-3-ol as a crude oil. This material was used without further purification.

EXAMPLE 103

Preparation of 5,6,7,8-tetrahydro-9-[(4-methoxyphenyl)methyl]-9H-dibenzo[b,d]pyrrol-3-ol Using the procedure of Example 100, the hydrogenation of 2.1 g of 1,2,3,4-tetrahydro-6-phenylmethoxy-9-[(4-methoxyphenyl)methyl]-9H-dibenzo[b,d]pyrrole from Example 88 produced crude 5,6,7,8-tetrahydro-9-[(4-methoxyphenyl)methyl]-9H-dibenzo[b,d]pyrrol-3-ol which was used without further purification.

EXAMPLE 104

Preparation of 5,6,7,8-tetrahydro-9-[(3,4-dimethoxyphenyl)methyl[-9H-dibenzo[b,d]pyrrol-3-ol Using the procedure of Example 100, the hydrogenation of 2.4 g of 1,2,3,4-tetrahydro-6-phenylmethoxy-9-[(3,4-dimethoxyphenyl) methyl]-9H-dibenzo[b,d]pyrrole from Example 81 produced 5,6,7,8-tetrahydro-9-[(3,4-dimethylphenyl)methyl]-9H-dibenzo[b,d]pyrrol-3-ol as a crude oil. This material was used without further purification.

EXAMPLE 105

Preparation of 5,6,7,8-tetrahydro-9-[(4-methylphenyl)methyl]-9H-dibenzo[b,d]pyrrol-3-ol Using the procedure of Example 100, the hydrogenation of 2.2 g of 1,2,3,4-tetrahydro-6-phenylmethoxy-9-[(4-methylphenyl)methyl]-9H-dibenzo[b,d]pyrrole from Example 82 gave 5,6,7,8-tetrahydro-9-[(4methylphenyl)methyl]-9H-dibenzo[b,d]pyrrol-3-ol as a crude oil which was used without further purification.

EXAMPLE 106

Preparation of 5,6,7,tetrahydro-9-[(2,4,6-trimethylphenyl)methyl-9H-dibenzo[b,d]pyrrol-3-ol Using the procedure of Example 100, the hydrogenation of 3.6 g of 1,2,3,4-tetrahydro-6-phenylmethoxy-9-[(2,4,6-trimethylphenyl) methyl]-9H-dibenzo[b,d]pyrrole from Example 83 produced 5,6,7,8-tetrahydro-9-[(2,4,6-trimethylphenyl)methyl]-9H-dibenzo[b,d]pyrrol-3-ol as a crude oil. This material was used without further purification.

EXAMPLE 107

Preparation of 5,6,7,8tetrahydro-1-(3-methoxyphenyl)-9-octyl-9H-dibenzo[b,d]pyrrol-3-ol Using the procedure of Example 86, 4.4 g of 5,6,7,8-tetrahydro-1-(3-methoxyphenyl)-6-phenylmethoxy-9H-dibenzo[b,d]pyrrole from Example 84 was hydrogenated giving 3.6 g (100%) of 5,6,7,8-tetrahydro-1-(3-methoxyphenyl)-9-octyl-9H-dibenzo[b,d]pyrrol-3-ol as a pale yellow oil.

EXAMPLE 108

Preparation of 5,6,7,8-tetrahydro-1,9-dioctyl-9H-dibenzo[b,d]pyrrol-3-ol

Using the procedure of Example 86, 2.3 g of 5,6,7,8-tetrahydro-1,9-dioctyl-6-phenylmethoxy-9H-dibenzo[b,d]pyrrole from Example 85 was hydrogenated giving 1.9 g (100%) of 5,6,7,8-tetrahydro-1,9-dioctyl-9H-dibenzo[b,d]pyrrol-3-ol as a yellow oil.

EXAMPLE 109

Preparation of 5-[(1,2,3,4-tetrahydro-9-octyl-9H-dibenzo[b,d]pyrrol-6yl)oxy]-2-furancarboxylic acid methyl ester To a slurry of 1.35 g of 60% NaH (dispersion in oil) suspended in 10 mL of dried DMSO a solution of 9.2 g of the phenol derivative from Example 86 in 90 mL of dried DMSO was added at room temperature over a 5 minute period. After 15 minutes of stirring, a solution of 5.8 g of 5-nitro-2-furanoic acid methyl ester[4] in 40 mL of dried DMSO was added at room temperature. The reaction mixture was stirred for an additional 5 hours, poured into water and ice and extracted with ethyl acetate. The organic phase was washed with water, dried over anhydrous magnesium sulfate and concentrated to give 13.9 g of a brown oil. Chromatographic purification on a silica gel column of this material afforded 10.2 g (78.6%) of 5-[(1,2,3,4-tetrahydro-9-octyl-9H-dibenzo[b,d]pyrrol-6-yl)oxy]-2-furancarboxylic acid methyl ester as a pale yellow oil.

EXAMPLE 110

Preparation of 5-[(1,2,3,4-tetrahydro-9-octyl-9H-dibenzo[b,d]pyrrol-7-yl)oxy]-2-furancarboxylic acid methyl ester Using the procedure of Example 109, 5.0 g of 5,6,7,8-tetrahydro-9-octyl-9H-dibenzo[b,d]pyrrol-2-ol from Example 87 was converted into 5-[(1,2,3,4-tetrahydro-9-octyl-9H-dibenzo[b,d]pyrrol-7-yl)oxy]-2-furancarboxylic acid methyl ester (6.3 g; 89.1%) as a yellow oil after chromatographic purification.

EXAMPLE 111

Preparation of 5-[(1,2,3,4-tetrahydro-1, dimethyl-9octyl-9H-dibenzo[b,d]pyrrol-6-yl)oxy]-2-furancarboxylic acid methyl ester Using the procedure of Example 109, 3.9 g of 5,6,7,8-tetrahydro-8,8-dimethyl-9-octyl-9H-dibenzo[b,d]pyrrol-3-ol from Example 88 was converted into 5-[(1,2,3,4-tetrahydro-9-octyl-9H-dibenzo[b,d]pyrrol-6-yl]oxy]-2-furancarboxylic acid methyl ester in 96.5% yield as a colorless oil after chromatographic purification.

EXAMPLE 112

Preparation of 5-[(1,2,3,4-tetrahydro-3,3-dimethyl-9-octyl-9H-dibenzo[b,d]pyrrol-6-yl)oxy]-2-furancarboxylic acid methyl ester Using the procedure of Example 109, 4.3 g of 5,6,7,8-tetrahydro-6,6-dimethyl-9-octyl-9H-dibenzo[b,d]pyrrol-3-ol from Example 89 was condensed with 2.6 g (15.2 mmol) of 5-nitro-2-methylfuroate to afford 5.1 g (86.0%) of 5-[(1,2,3,4-tetrahydro-3,3-dimethyl-9-octyl-9H-dibenzo[b,d]pyrrol-6-yl)oxy]-2-furancarboxylic acid methyl ester after chromatographic purification as a yellow oil.

EXAMPLE 113

Preparation of 5-[(1,2,3,4-tetrahydro-9-butyl-9H-dibenzo[b,d]pyrrol-6-yl) oxy]-2-furan carboxylic acid methyl ester Using the procedure of Example 109, 3.8 g of 5,6,7,8-tetrahydro-9-butyl-9H-dibenzo[b,d]pyrrol-3-ol from Example 90 was converted into 5-[(1,2,3,4-tetrahydro-9-butyl-9H-dibenzo[b,d]pyrrol-6-yl)oxy]-2-furancarboxylic acid methyl ester (4.5 g; 78.5%) as a yellow oil after chromatographic purification.

EXAMPLE 114

Preparation of 5-[[1,2,3,4-tetrahydro-9-(4bromophenyl)methyl-9H-dibenzo[b,d]pyrrol-6-yl]oxy]-2-furancarboxylic acid methyl ester Using the procedure of Example 109, 2.4 g of 5,6,7,8-tetrahydro-9-(4-bromophenyl)methyl-9H-dibenzo[b,d]pyrrol-3-ol from Example 91 was converted into 5-[[1,2,3,4-tetrahydro-9-(4-bromophenyl)methyl-9H-dibenzo[b,d]pyrrol-6-yl]oxy]-2-furancarboxylic acid methyl ester (1.4 g; 43.3%) as a yellow oil after chromatographic purification.

EXAMPLE 115

Preparation of 5-[(1,2,3,4-tetrahydro-9-methyl-9H-dibenzo[b,d]pyrrol-6-yl)oxy]-2-furancarboxylic acid methyl ester Using the procedure of Example 109, 3,4 g of 5,6,7,8-tetrahydro-9-methyl-9H-dibenzo[b,d]pyrrol-3-ol from Example 92 was converted into 5-[(1,2,3,4-tetrahydro-9-methyl-9H-dibenzo[b,d]pyrrol-6-yl)oxy]-2-furancarboxylic acid methyl ester (3.6 g; 65.5%) as a yellow oil after chromatographic purification.

EXAMPLE 116

Preparation of 5-[[1,2,3,4-tetrahydro-9-(4-chlorophenyl)methyl-9H-dibenzo[b,d]pyrrol-6-yl]-oxy]-2-furancarboxylic acid methyl ester Using the procedure of Example 109, 5.6 g of 5,6,7,8-tetrahydro-9-(4-chlorophenyl)methyl-9H-dibenzo[b,d]pyrrol-3-ol from Example 93 was converted into 5-[[1,2,3,4-tetrahydro-9-(4-chlorophenyl)methyl-9H-dibenzo[b,d]pyrrol-6-yl]oxy]-2-furancarboxylic acid methyl ester (7.2 g; 91.9%) as an orange oil after chromatographic purification.

EXAMPLE 117

Preparation of 5-[(1,2,3,4-tetrahydro-9-heptyl-9H-dibenzo[b,d]pyrrol-6yl)oxy]-2-furancarboxylic acid methyl ester Using the procedure of Example 109, 4.9 g of 5,6,7,8-tetrahydro-9-heptyl-9H-dibenzo[b,d]pyrrol-3-ol from Example 94 was converted into 5-[(1,2,3,4-tetrahydro-9-heptyl-9H-dibenzo[b,d]pyrrol-6-yl)oxy]-2-furancarboxylic acid methyl ester (6.3 g; 89.6%) as a yellow oil after chromatographic purification.

EXAMPLE 118

Preparation of 5-[(1,2,3,4-tetrahydro-9-nonyl-9H-dibenzo[b,d]pyrrol-6-yl)oxy]-2-furancarboxylic acid methyl ester Using the procedure of Example 109, 4.7 g of 5,6,7,8-tetrahydro-9-nonyl-9H-dibenzo[b,d]pyrrol-3-ol from Example 95 was converted into 5-[(1,2,3,4-tetrahydro-9-nonyl-9H-dibenzo[b,d]pyrrol-6-yl)oxy]-2-furancarboxylic acid methyl ester (5.1 g; 77.7%) as a yellow oil after chromatographic purification.

EXAMPLE 119

Preparation of 5-[(1,2,3,4-tetrahydro-9-dodecyl-9H-dibenzo[b,d]pyrrol-6-yl)oxy]-2-furancarboxylic acid methyl ester Using the procedure of Example 109, 5.2 g of 5,6,7,8-tetrahydro-9-dodecyl-9H-dibenzo[b,d]pyrrol-3-ol from Example 96 was converted into 5-[(1,2,3,4-tetrahydro-9-dodecyl-9H-dibenzo[b,d]pyrrol-6-yl)oxy]-2-furancarboxylic acid methyl ester (6.1 g; 85.9%) as a yellow oil after chromatographic purification.

EXAMPLE 120

Preparation of 5-[[1,2,3,4tetrahydro-9-(4-heptylphenyl)-methyl-9H-dibenzo[b,d]pyrrol-6-yl]oxy]-2-furancarboxylic acid methyl ester Using the procedure of Example 109, 3.7 g of 5,6,7,8-tetrahydro-9-(4-heptylphenyl)methyl-9H-dibenzo[b,d]pyrrol-3-ol from Example 97 was converted into 5-[[1,2,3, 4-tetrahydro-9-(4-heptylphenyl)methyl-9H-dibenzo[b,d]pyrrol-6-yl]oxy]-2-furancarboxylic acid methyl ester (3.1 g; 63.2%) as a yellow oil after chromatographic purification.

EXAMPLE 121

Preparation of rac-5-[[1,2,3,4-tetrahydro-9-(3,7-dimethyloctyl)-9H-dibenzo[b,d]pyrrol-6-yl]oxy]-2-furancarboxylic acid methyl ester Using the procedure of Example 109, 6.7 g of 5,6,7,8-tetrahydro-9-(3,7-dimethyloctyl)-9H-dibenzo[b,d]pyrrol-3-ol from Example 98 was condensed with 3.9 g of 5-nitro-2-furanoic acid methyl ester to produce 7.1 g (76.6%) of rac-5-[[9-(3,7-dimethyl-octyl) -1,2,3,4-tetrahydro-9H-dibenzo[b,d]pyrrol-6-yl]oxy]-2-furancarboxylic acid methyl ester as a yellow viscous oil after chromatographic purification.

EXAMPLE 122

Preparation of -5-[[-1,2,3,4-tetrahydro-9-(4-phenylbutyl)-9H-dibenzo[b,d]pyrrol-6-yl]oxy]-2-furancarboxylic acid methyl ester Using the procedure of Example 109, 4.2 g of 5,6,7,8-tetrahydro-9-(4-phenylbutyl)-9H-dibenzo[b,d]pyrrrol-3-ol from Example 99 was condensed with 2.6 g of 5-nitro-2-furanoic acid methyl ester to afford 4.6 g (77.4%) of 5-[[1,2,3,4-tetrahydro-9-(4-phenylbutyl)-9H-dibenzo[b,d]pyrrol-6-yl]oxy]-2-furan carboxylic acid methyl ester as a yellow oil after chromatographic purification.

EXAMPLE 123

Preparation of 1,2,3,4-tetrahydro-5-[[9-[(4-fluorophenyl)methyl]-9H-dibenzo[b,d]pyrrol -6-yl]oxy]-2-furancarboxylic acid methyl ester A solution of approximately 7.25 mmol of 5,6,7,8-tetrahydro-9-[(4-fluorophenyl)methyl]-9H-dibenzo[b,d]pyrrol-3-ol as a crude oil from Example 100 in 20 ml of dimethyl sulfoxide was added dropwise to a freshly prepared suspention of 0.35 g of sodium hydride (55% dispersion in mineral oil) in 2 ml dimethylsulfoxide at room temperature and under argon. The resulting mixture was stirred an additional 15 minutes and a solution of methyl 5-nitro-2-furoate (1.37 g) in dimethylsulfoxide (10 mL) was added. The black mixture was stirred an additional 2 hours and poured into ice and water containing a few drops of acetic acid. The product was extracted with dichloromethane and the organic layer was washed with water, dried over anhydrous sodium sulfate, and evaporated. The residue was purified by HPLC eluting with ethyl acetate-hexane (1:9) and crystallized from ether-hexane. 2.2 g (72%) of 1,2,3,4-tetrahydro-5-[[9-[(4-fluorophenyl)methyl]-9H-dibenzo[b,d]pyrrol-6-yl]oxy]-2-furancarboxylic acid methyl ester was obtained as a colorless crystalline material, mp 85°–86° C.

Anal. Calcd. for $C_{25}H_{22}FNO_4$: C, 71.59; H, 5.29; N, 3.34; F, 4.53. Found: C, 71.35; H, 5.37; N, 3.16; F, 4.63.

EXAMPLE 124

Preparation of 1,2,3,4-tetrahydro-5-[[9-[(3-Fluorophenyl)methyl]-9H-dibenzo[b,d]pyrrol-6-yl]oxy]-2-furancarboxylic acid methyl ester Using the procedure of Example 123 a solution of approximately 7.25 mmol of 5,6,7,8-tetrahydro-9[(3-fluorophenyl) methyl]-9H-dibenzo[b,d]pyrrol-3-ol from Example 101 was treated with 1.37 g of methyl 5-nitro-2-furanoate. Purification by HPLC (eluting system ethyl acetate-hexane 1:4) and crystallization from ethyl ether-hexane afforded 2.3 g (76%) of 5-[[9-[(3-fluorophenyl) methyl]-1,2,3,4-tetrahydro-9H-dibenzo[b,d]pyrrol-6-yl]oxy]-2-furancarboxylic acid methyl ester as a colorless crystalline material, mp 86°–88° C.

Anal, Calcd for $C_{25}H_{22}FNO_4$: C, 71.59; H, 5.29; N, 3.34; F, 4.53. Found: C, 71.84; H, 5.44; N, 3.31; F, 4.64.

EXAMPLE 125

Preparation of 5-[[1,2,3,4-tetrahydro-9-[(2-Fluorophenyl)methyl]-9H-dibenzo[b,d]pyrrol-6-yl]oxy]-2-furancarboxylic acid methyl ester A solution of approximately 7 mmol of 5,6,7,8-tetrahydro-9[(2-fluorophenyl) methyl]-9H-dibenzo[b,d]pyrrol-3-ol from Example 102 was treated with 5-nitro-2-furanoic acid methyl ester (1.37 g) as described in Example 123. The crude product was purified by HPLC eluted with ethyl acetate-hexane (1:9) and crystallized from ethyl ether-hexane to give 2.3 g (78%) of 5-[[9-[(2-fluorophenyl) methyl]-1,2,3,4-tetrahydro-9H-dibenzo[b,d]pyrrol-6-yl]oxy]-2-furancarboxylic acid methyl ester as a colorless crystalline material, mp 121°–122° C.

Anal, Calcd. for $C_{25}H_{22}FNO_4$: C, 71.59; H, 5.29; N, 3.34; F, 4.53. Found: C, 71.57; H, 5.30; N, 3.32; F, 4.65.

EXAMPLE 126

Preparation of 5-[[1,2,3,4-Tetrahydro-9-[(4-methoxyphenyl)methyl]-9H-dibenzo[b,d]pyrrol-6-yl]oxy]-2-furancarboxylic acid methyl ester A solution of approximately 5.3 mmol of 5,6,7,8-tetrahydro-9-[(4-methoxyphenyl)methyl]-9H-dibenzo[b,d]pyrrol-3-ol from Example 103 was treated with 5-nitro-2-furanoic acid methyl ester (1.03 g) as described in Example 123. The crude product was purified by HPLC (eluting system: ethyl acetate-hexane 1:6) and crystallized from ethyl ether-hexane to provide 1.6 g (70%) of colorless crystals of 5-[[1,2,3,4-tetrahydro-9-[(4-methoxyphenyl) methyl]-9H-dibenzo[b,d]pyrrol-6-yl]oxy]-2-furancarboxylic acid methyl ester, mp 79°–80° C.

Anal. Calcd. for $C_{26}H_{25}NO_5$: C, 72.37; H, 5.84; N, 3.25. Found: C, 72.32; H, 5.88; N, 3.22.

EXAMPLE 127

Preparation of 5-[[1,2,3,4-Tetrahydro-9-[(3,4-dimethoxyphenyl) methyl]-9H-dibenzo[b,d]pyrrol-6-yl]oxy]-2-furancarboxylic acid methyl ester A solution of approximately 5.6 mmol of 5,6,7,8-tetrahydro-9[(3,4-dimethoxyphenyl)methyl]-9H-dibenzo[b,d]pyrrol-3-ol from Example 104 was treated with 5-nitro-2-furanoic acid methyl ester (1.03 g) as described in Example 123. The crude product was purified by HPLC (eluting system: ethyl acetate-hexane 1:4) and crystallized from ethyl ether-hexane to provide 2.2 g (85%) of 5-[[9-[(3,4-dimethoxyphenyl)methyl]-1,2,3,4-tetrahydro-9H-dibenzo[b,d]pyrrol-6-yl]oxy]-2-furancarboxylic acid methyl ester as colorless crystals, mp 100°–101° C.

Anal. Calcd. for $C_{27}H_{27}NO_6$: C, 70.27; H, 5.90; N, 3.03. Found: C, 70.50; H, 5.76; N, 3.06.

EXAMPLE 128

Preparation of 5-[[1,2,3,4-Tetrahydro-9-[(4-methylphenyl)methyl]-9H-dibenzo[b,d]pyrrol-6-yl]oxy]-2-furancarboxylic acid methyl ester A solution of approximately 5.8 mmol of 5,6,7,8-tetrahydro-9-[(4-methylphenyl) methyl]-9H-dibenzo[b,d]pyrrol-3-ol from Example 105 was treated with 5-nitro furanoic acid methyl ester (1.03 g) as described in Example 123. The crude product was purified by HPLC (eluting system: ethyl acetate-hexane 1:9) and crystallized from ethyl ether-hexane to provide 1.9 g (79%) of 5-[[1,2,3,4-tetrahydro-9-[(4-methylphenyl)methyl]-9 H-dibenzo[b,d]pyrrol-6-yl]oxy]-2-furancarboxylic acid methyl ester as a colorless crystalline material, mp 80°–81° C.

Anal, Calcd. for $C_{26}H_{25}NO_4$: C, 75.16; H, 6.06; N, 3.37. Found: C, 75.09; H, 6.11; N, 3.33.

EXAMPLE 129

Preparation of 5-[[1,2,3,4-Tetrahydro-9-[(2,4,6-trimethylphenyl) methyl]-9H-dibenzo[b,d]pyrrol-6-yl]oxy-2-furancarboxylic acid methyl ester A solution of approximately 9.3 mmol of 5,6,7,8-tetrahydro-9[(2,4,6-trimethylphenyl)methyl]-9H-dibenzo[b,d]pyrrol-3-ol from Example 106 was treated with 5-nitro-2-furanoic acid methyl ester (2.05 g) as described in Example 123. The crude product was purified by HPLC (eluting system ethylacetate-hexane 1:9) and crystallized from dichloromethane-hexane to provide 2.9 g (70%) of colorless crystals of 5-[[1,2,3,4-tetrahydro-9-[(2,4,6-trimethylphenyl) methyl]-9H-dibenzo[b,d]pyrrol-6-yl]oxy]-2-furancarboxylic acid methyl ester, mp 116°–117° C.

Anal, Calcd. for $C_{28}H_{29}NO_4$: C, 75.82; H, 6.59; N, 3.16. Found: C, 75.57; H, 6.64; N, 3.12.

EXAMPLE 130

Preparation of 5-[[1,2,3,4--tetrahydro-1-(3-methoxyphenyl)-9-octyl-9H-dibenzo[b,d]pyrrol-6-yl]oxy]-2-furancarboxylic acid methyl ester Using the procedure of Example 123, 3.6 g (8.9 mmol) of 5,6,7,8-tetrahydro-1-(3-methoxyphenyl)-9-octyl-9H-dibenzo[b,d]pyrrol-3-ol from Example 107 was condensed with 1.6 g of 5-nitro-2-furanoic acid methyl ester to afford 3.2 g (49%) of 5-[[1,2,3,4tetrahydro-1-(3-methoxyphenyl)-9octyl-9 H-dibenzo[b,d ]pyrrol-6yl]oxy]-2-furancarboxylic acid methyl ester as a pale yellow oil after chromatographic purification

EXAMPLE 131

Preparation of rac-5-[[1,2,3,4-tetrahydro-1,9-dioctyl-9H-dibenzo[b,d]pyrrol-6-yl]oxy]2-furancarboxylic acid methyl ester Using the procedure of Example 123, 2.3 g of 5,6,7,8-tetrahydro-1,9-dioctyl-9H-dibenzo[b,d]pyrrol-6-yl]oxy]]pyrrol-3-ol from Example 108 was condensed with 1.1 g of 5-nitro-2-furanoic acid methyl ester to provide 1.2 g (40.2%) of rac-5-[[1,2,3,4-tetrahydro-1,9-dioctyl-9H-dibenzo[b,d]pyrrol-6-yl]oxy]-2-furancarboxylic acid methyl ester as a yellow oil

EXAMPLE 132

Preparation of 5-[(1,2,3,4-tetrahydro-9-octyl-9H-dibenzo[b,d]pyrrol-6-yl)oxy]-2-furancarboxylic acid The hydrolysis of the methyl ester was carried out with 87% aqueous KOH in methanol and water by using the procedure described in Example 43. In this manner 10.2 g of ester obtained from Example 109 was converted into 5-[(1,2,3,4-tetrahydro-9-octyl-9H-dibenzo[b,d]pyrrol-6-yl)oxy]-2-furancarboxylic acid (7.5 g) in 76% yield as a white solid after crystallization from ethyl acetate-hexane, mp 130°–132° C.

Anal. calcd for $C_{25}H_{31}NO_4$: C, 73.32; H, 7.63; N, 3,42. Found: C, 73.66; H, 7.60; N, 3.32.

EXAMPLE 133

Preparation of 5-[(1,2,3,4-tetrahydro-9-octyl-9H-dibenzo[b,d]pyrrol-7-yl) oxy]-2-furancarboxylic acid Using the procedure of Example 43, 6.3 g of the methyl ester from Example 110 was saponified to 5-(1,2,3,4-tetrahydro-9-octyl-9H-dibenzo[b,d]pyrrol-7-yl)oxy]-2-furancarboxylic acid (4.3 g; 70.6%) as a white solid after crystallization from ethyl acetate, mp 142°–144° C.

Anal. calcd for $C_{25}H_{31}NO_4$: C, 73.32; H, 7.63; N, 3,42. Found: C, 73.34; H, 7.56; N, 3.19.

EXAMPLE 134

Preparation of 5-[(1,2,3,4-tetrahydro-1,1-dimethyl-9-octyl-9H-dibenzo[b,d]pyrrol-6-yl)oxy]-2-furancarboxylic acid Using the procedure of Example 43, 5.2 g of methyl ester from Example 111 was saponified to 5-[(1,2,3,4-tetrahydro-1,1-dimethyl-9-octyl-9H-dibenzo[b,d]-pyrrol-6-yl)oxy]-2-furancarboxylic acid (2.4 g) in 47.5% yield as a white solid after crystallization from ethyl acetate-hexane, mp 118.0°–119.5° C.

Anal. calcd for $C_{27}H_{35}NO_4$: C, 74.11; H, 8.06; N, 3.20. Found: C, 74.17; H, 8.27; N, 3.10.

EXAMPLE 135

Preparation of 5-[(,1,2,3,4-tetrahydro-3,3-dimethyl-9-octyl-9H-dibenzo[b,d]pyrrol-6-yl)oxy]-2-furancarboxylic acid Using the procedure of Example 43, 5.1 g of methyl ester from Example 112 was hydrolyzed to 5-[(1,2,3,4-tetrahydro-3,3-dimethyl-9-octyl-9H-dibenzo[b,d]pyrrol-6-yl)oxy]-2-furancarboxylic acid (3.3 g) in 66.8% yield as a white solid after repeated crystallizations from ethyl acetate, mp 152.5°–153.5° C.

Anal. Calcd. for $C_{27}H_{35}NO_4$: C, 74.11; H, 8.06; N, 3.20. Found: C, 74.17; H, 7.90; N, 3.20.

EXAMPLE 136

Preparation of 5-[(1,2,3,4-tetrahydro-9-butyl-9H-dibenzo[b,d[pyrrol-6-yl)oxy]-2-furan carboxylic acid Using the procedure of Example 43, 4.5 g of the methyl ester from Example 113 was hydrolyzed to 5-[(1,2,3,4-tetrahydro-9-butyl-9H-dibenzo[b,d]pyrrol-6-yl)oxy]-2-furancarboxylic acid (2.1 g; 48.5%) as a white solid after repeated crystallizations from ethyl acetate, mp 147.5°–149.0° C.

Anal. Calcd for $C_{21}H_{23}NO_4$: C, 71.73; H, 6.56; N, 3.96. Found: C, 71.27; H, 6.53; N, 3.94.

EXAMPLE 137

Preparation of 5-[[1,2,3,4-tetrahydro-9(4-bromophenyl)methyl-9H-dibenzo[b,d]pyrrol-6-yl]oxy]-2-furancarboxylic acid A solution of the methyl ester (0.9 g) from Example 114 in 10 mL of tetrahydrofuran was treated with a solution of 0.8 g of LiOH.H₂O in 10 mL water. The reaction mixture was stirred at room temperature for 28 h, diluted with water, acidified with 2N-HCl and extracted with ethyl acetate. The organic phase was washed with saturated brine, dried over anhydrous magnesium sulfate and concentrated in vacuo to give 5-[[1,2,3,4-tetrahydro-9-(4-bromophenyl)methyl-9H-dibenzo[b,d]pyrrol-6-yl]oxy]-2-furancarboxylic acid (0.35 g; 40.0%) as a white solid after repeated crystallizations from ethyl acetate, mp 155.5°–157.5° C.

Anal. Calcd for $C_{24}H_{20}BrNO_4$: C, 61.82; H, 4.32; N, 3.00. Found: C, 61.92; H, 4.45; N, 2.88.

EXAMPLE 138

Preparation of 5-[(1,2,3,4-tetrahydro-9-methyl-9H-dibenzo[b,d]pyrrol-6-yl)oxy]-2-furancarboxylic acid Using the procedure of Example 43, 3.6 g of the methyl ester from Example 115 was saponified to 5-[(1,2,3,4-tetrahydro-9-methyl-9H-dibenzo[b,d]pyrrol-6-yl)oxy]-2-furancarboxylic acid (1.0 g; 29.1%) as a white solid after repeated crystallization from ethyl acetate, mp 150.0°–151.5° C.

Anal. Calcd for $C_{18}H_{17}NO_4$: C, 69.44; H, 5.50; N, 4.50. Found: C, 69.33; H, 5.54; N, 4.39.

EXAMPLE 139

Preparation of 5-[[1,2,3,4-tetrahydro-9-(4-chlorophenyl)methyl-9H-dibenzo[b,d]pyrrol-6yl]-oxy]-2-furancarboxylic acid Using the procedure of Example 43, 7.2 g of the methyl ester from Example 111 was hydrolyzed to 5-[[1,2,3,4-tetrahydro-9-(4-chlorophenyl) methyl-9H-dibenzo[b,d]pyrrol-6-yl]oxy]-2-furancarboxylic acid (2.4 g; 57.3%) as a pale yellow solid after purification on activated charcoal and crystallization from ethyl acetate, mp 162.5°–164.0° C.

Anal. Calcd for $C_{24}H_{20}ClNO_4$: C, 68.33; H, 4.78; N, 3.32. Found: C, 68.40; H, 4.53; N, 3.24.

EXAMPLE 140

Preparation of -5-[(1,2,3,4-tetrahydro-9-heptyl-9H-dibenzo[b,d]pyrrol-6-yl)oxy]-2-furancarboxylic acid Using the procedure of Example 43, 6.3 g of the methyl ester from Example 117 was saponified to 5-(1,2,3,4-tetrahydro-9-heptyl-9H-dibenzo[b,d]pyrrol-6-yl)oxyl-2-furancarboxylic acid (4.1 g; 67.4%) as a white solid after repeated crystallizations from ethyl acetate, mp 128.0°–129.5° C.

Anal. Calcd for $C_{24}H_{29}NO_4$: C, 72.89; H, 7.39; N, 3.54. Found: C, 72.61; H, 7.66; N, 3,40.

EXAMPLE 141

Preparation of 5-[(1,2,3,4-tetrahydro-9-dodecyl-9H-dibenzo[b,d]pyrrol-6-yl)oxy]-2-furancarboxylic acid Using the procedure of Example 43, 6.1 g of the methyl ester from Example 118 was hydrolyzed to 5-[(1,2,3,4-tetrahydro-9-dodecyl- H-dibenzo[b,d]pyrrol-6-yl)oxy]-2-furancarboxylic acid (3.2 g; 54.0%) as a white solid after repeated crystallizations from ethyl acetate-hexane, mp 109.5°–111.5° C.

Anal. Calcd for $C_{29}H_{39}NO_4$: C, 74.81; H, 8.44; N, 3.01. Found: C, 75.05; H, 8.69; N, 2.95.

EXAMPLE 142

Preparation of 5-[(1,2,3,4-tetrahydro-9-nonyl-9H-dibenzo[b,d]pyrrol-6-yl)oxy]-2-furancarboxylic acid Using the procedure of Example 43, 5.1 g of the methyl ester of Example 119 was saponified to 5-[(1,2,3,4-tetrahydro-9-nonyl-9H-dibenzo[b,d]pyrrol-6-yl)oxy]-2-furancarboxylic acid (3.9 g; 79.1%) as a white solid after crystallization from ethyl acetate-hexane, mp 130.0°–131.5° C.

Anal. Calcd for $C_{26}H_{33}NO_4$: C, 73.73; H, 7.85; N, 3.31. Found: C, 73.57; H, 7.95; N, 3.15.

EXAMPLE 143

Preparation of 5-[[1,2,3,4-tetrahydro-9-(4-heptylphenyl)methyl-9H-dibenzo[b,d]pyrrol-6-yl]oxy]-2-furancarboxylic acid Using the procedure of Example 43, 3.1 g of the methyl ester of Example 120 was saponified to 5-[[1,2,3,4-tetrahydro-9-(4-heptyl-phenyl)methyl-9H-dibenzo[b,d]pyrrol -6yl]oxy]-2-furancarboxylic acid (2.3 g; 76.4%) as a white solid after crystallization from ethyl acetate, mp 163.5°–165.0° C.

Anal. Calcd for $C_{31}H_{35}NO_4$: C, 76.67; H, 7.26; N, 2.88. Found: C, 76.45; H, 7.34; N, 2.76.

EXAMPLE 144

Preparation of rac-5-[[1,2,3,4-tetrahydro 9-(3,7-dimethyloctyl)-9H-dibenzo[b,d]pyrrol-6-yl]oxy]-2-furancarboxylic acid Using the procedure of Example 43, 7.1 g of the methyl ester from Example 121 was hydrolyzed to rac-5-[[1,2,3,4-tetrahydro-9-(3,7-dimethyloctyl)-9H-dibenzo[b,d]pyrrol-6-yl]oxy]-2-furancarboxylic acid (3.9 g; 56.7%) as a white crystalline material after repeated crystallizations from ethyl acetate-hexane, mp 98.5°14 100.5° C.

Anal, Calcd. for $C_{27}H_{35}NO_4$: C, 74.11; H, 8.06; N, 3.20. Found: C, 74.21; H, 8.12; N, 3.12.

EXAMPLE 145

Preparation of 5-[[1,2,3,4-tetrahydro-9-(4-phenylbutyl)-9H-dibenzo[b,d]pyrrol-6-yl]oxy]-2-furancarboxylic acid Using the procedure of Example 43, 4.6 g of the methyl ester from Example 122 was hydrolyzed to 5-[[1,2,3,4-tetrahydro-9-(4-phenylbutyl) -9H-dibenzo[b,d]pyrrol-6-yl]oxy]-2-furancarboxylic acid (3.1 g; 69.7%) as a white solid after repeated crystallizations from ethyl acetate-hexane, mp 119.5°–121° C.

Anal. Calcd. for $C_{27}H_{27}NO_4$: C, 75.50; H, 6.34; N, 3.26. Found: C, 75.43; H, 6.28; N, 3.14.

EXAMPLE 146

Preparation of 5-[[1,2,3,4-tetrahydro-9-[(4-fluorophenyl)methyl]-9H-dibenzo[b,d]pyrrol-6-yl]-oxy]-2-furancarboxylic acid A solution of 5-[[9-[(4-fluorophenyl)methyl]-1,2,3,4-tetrahydro-9H-dibenzo[b,d]pyrrol-6-yl]oxy]-2-furancarboxylic acid methyl ester (2.1 g) from Example 123 in tetrahydrofuran (20 mL) and methanol (10 mL) was treated with 1N sodium hydroxide solution (6 mL) and refluxed for 90 minutes. The reaction mixture was diluted with water, treated with excess 2N hydrochloric acid (4 mL) and the product extracted with dichloromethane. The organic layer was washed with water, dried over anhydrous sodium sulfate, evaporated in vacuo, and crystallized from dichloromethane-hexane to provide 1.7 g (84%) of 5-[[9-[(4-fluorophenyl)methyl]-1,2,3,4-tetrahydro-9H-dibenzo[b,d]pyrrol-6-yl]oxy]-2-furancarboxylic acid as a colorless crystalline material, mp at 161° C. with decomposition.

Anal Calcd. for $C_{24}H_{20}FNO_4$: C, 71.10; H, 4.97; N, 3,45; F, 4.69. Found: C, 70.95; H, 4.89; N, 3,42; F, 4.73.

EXAMPLE 147

Preparation of 5-[[1,2,3,4-tetrahydro-9-[(3-fluorophenyl)methyl]-9H-dibenzo[b,d]pyrrol-6-yl]oxy]-2-furancarboxylic acid Using the procedure of Example 146, 5-[[1,2,3,4-tetrahydro-9-[(3-fluorophenyl) methyl]-9H-dibenzo[b,d]pyrrol-6-yl]oxy]-2-furancarboxylic acid methyl ester (2 g) from Example 124 was hydrolyzed to the corresponding acid. Crystallization from dichloromethane-hexane provided 1.6 g (82%) of 5-[[9-[(3-fluorophenyl)methyl]-1,2,3,4-tetrahydro-9H-dibenzo[b,d]pyrrol-6-yl]oxy]-2-furancarboxylic acid as colorless crystals, mp at 158° C. with decomposition.

Anal. Calcd. for $C_{24}H_{20}FNO_4$: C, 71.10; H, 4.97; N, 3,45; F, 4.69. Found: C, 70.76; H, 4.80; N, 3.21; F, 4.88.

EXAMPLE-148

Preparation of 5-[[1,2,3,4-tetrahydro-9-[(2-fluorophenyl)methyl]-9H-dibenzo[b,d]pyrrol-6-yl]oxy]-2-furancarboxylic acid Using the procedure of Example 146, 5-[[1,2,3,4-tetrahydro-9-[(2-fluorophenyl) methyl]-9H-dibenzo[b,d]pyrrol-6-yl]oxy]-2-furancarboxylic acid methyl ester (2.3 g) from Example 125 was hydrolyzed to the corresponding acid. Crystallization from dichloromethane-hexane provided 2.2 g (98%) of 5-[[9-[(2-fluorophenyl)methyl]-1,2,3,4-tetrahydro-9 H-dibenzo[b,d]pyrrol-6-yl]oxy ]-2-furan carboxylic acid as a colorless crystalline material, mp at 168° C. with decomposition.

Anal. Calcd. for $C_{24}H_{20}FNO_4$: C, 71.10; H, 4.97; N, 3,45; F, 4.69. Found: C, 71.12; H, 4.95; N, 3.39; F, 4.89.

EXAMPLE 149

Preparation of 5-[[1,2,3,4-tetrahydro-9-[(4-methoxyphenyl)methyl]-9H-dibenzo[b,d]pyrrol-6-yl]oxy]-2-furancarboxylic acid Using the procedure of Example 146, 5-[[1,2,3,4-tetrahydro-9[(4-methoxy phenyl)methyl]-9H-dibenzo[b,d]pyrrol-6-yl]oxy]-2-furancarboxylic acid methyl ester(1.6 g) from Example 126 was hydrolyzed to the corresponding acid. Crystallization from dichloromethane-hexane provided 1.5 g (97%) of 5-[[1,2,3,4-tetrahydro-9-[(4-methoxyphenyl)methyl]-9 H-dibenzo[b,d]pyrrol-6-yl]oxy]-2-furan carboxylic acid as a colorless crystalline material, mp at 180° C. with decomposition.

Anal, Calcd. for $C_{25}H_{23}NO_5$: C, 71.93; H, 5.55; N, 3.36. Found: C, 71.78; H, 5.36; N, 3.18.

EXAMPLE 150

Preparation of 5-[[1,2,3,4-tetrahydro-9-[(3,4-dimethoxyphenyl) methyl]-9H-dibenzo[b,d]pyrrol-6-yl]oxy]-2-furancarboxylic acid Using the procedure of Example 146, 5-[[1,2,3,4-tetrahydro-9[(3,4-dimethoxy phenyl)methyl]-9H-dibenzo[b,d]pyrrol-6-yl]oxy]-2-furancarboxylic acid methyl ester (2 g) from Example 127 was hydrolyzed to the corresponding acid. Crystallization from dichloromethane-hexane provided 1.9 g (98%) of 5-[[1,2,3,4-tetrahydro-9-[(3,4-dimethoxyphenyl)methyl]-9H-dibenzo[b,d]pyrrol-6-yl]oxy]-2-furancarboxylic acid as a colorless crystalline material, mp at 171° C. with decomposition.

Anal, Calcd. for $C_{26}H_{25}NO_6$: C, 69.79; H, 5.63; N, 3.13. Found: C, 69.92; H, 5.64; N, 3.04.

EXAMPLE 151

Preparation of 5-[[1,2,3,4-tetrahydro-9-[(4-methylphenyl)methyl[-9H-dibenzo[b,d]pyrrol-6-yl]oxy]-2-furancarboxylic acid Using the procedure of Example 146, 5-[[1,2,3,4-tetrahydro-9[(4-methylphenyl)methyl]-9 H-dibenzo[b,d]pyrrol-6-yl]oxy]-2-furancarboxylic acid methyl ester (1.8 g) from Example 128 was hydrolyzed to the corresponding acid. Crystallization from dichloromethane-hexane provided 1.65 g (95%) of 5-[[1,2,3,4-tetrahydro-9-[(4-methylphenyl)methyl]-9H-dibenzo[b,d]pyrrol-6-yl]oxy]-2-furancarboxylic acid as a colorless crystalline material, mp at 168° C. with decomposition.

Anal. Calcd. for $C_{25}H_{23}NO_4$: C, 74.80; H, 5.77; N, 3,49. Found: C, 74.71; H, 5.59; N, 3.34.

EXAMPLE 152

Preparation of 5-[[-1,2,3,4-Tetrahydro-9-[(2,4,6-trimethylphenyl) methyl]-9H-dibenzo[b,d]pyrrol-6-yl]oxy]-2-furancarboxylic acid Using the procedure of Example 146, 5-[[1,2,3,4-tetrahydro-9-[(2,4,6-trimethylphenyl)methyl]-9 H-dibenzo[b,d]pyrrol-6-yl]oxy]-2-furancarboxylic acid methyl ester (2.7 g) from Example 129 was hydrolyzed to the corresponding acid. Crystallization from acetone provided 2 g (78%) of 5-[[1,2,3,4-tetrahydro-9-[(2,4,6-trimethylphenyl)methyl]-9H-dibenzo[b,d]pyrrol-6-yl]oxy]-2-furancarboxylic acid as a colorless crystalline material, mp at 210° C. with decomposition.

Anal, Calcd. for $C_{27}H_{27}NO_4$: C, 75.50; H, 6.34; N, 3.26. Found: C, 75.23; H, 6.29; N, 3.09.

EXAMPLE 153

Preparation of rac-5-[[1,2,3,4-tetrahydro-1-(3-methoxyphenyl)-9-octyl-9H-dibenzo[b,d]pyrrol-6-yl]oxy]-2-furancarboxylic acid Using the procedure of Example 137, 3.2 g of the methyl ester from Example 130 was saponified to 1.9 g (61%) of rac-5-[[1,2,3,4-tetrahydro-1,9-dioctyl-9H-dibenzo[b,d]pyrrol-6-yl]oxy]-2-furancarboxylic acid as a white foam.

Anal. Calcd. for $C_{33}H_{47}NO_4$: C, 74.54; H, 7.23; N, 2.72. Found: C, 74.47; H, 7.21; N, 2.64.

EXAMPLE 154

Preparation of rac-5-[(1,2,3,4-tetrahydro-1,9-dioctyl-9H-dibenzo[b,d]pyrrol-6-yl)oxy]-2-furancarboxylic acid Using the procedure of Example 137, 1.2 g of the methyl ester from Example 131 was hydrolyzed to 0.9 g (77.5%) of rac-5-[(1,2,3,4-tetahydro-1,9-dioctyl-9H-dibenzo[b,d]pyrrol-6-yl)oxy]-2-furancarboxylic acid as a white solid, mp 107.5°–109° C.

Anal. Calcd. for $C_{33}H_{47}NO_4$: C, 75.97; H, 9.08; N, 2.68. Found: C, 76.22; H, 9.18; N, 2.52.

EXAMPLE 155

Preparation of 5-[(-1,2,3,4-tetrahydro-9-octyl-9H-dibenzo[b,d]pyrrol-6-yl)carbonyl]-2-furancarboxaldehyde A solution of 8.1 g of 2-[(2-furanyl-1,3-dimethyl]-imidazolidine[3] in 90 mL of THF was treated with 30 mL of 1.6M n-butyllithium solution in hexane at −75° C. After 15 minutes of stirring a solution of 12 g of 5,6,7,8-tetrahydro-9-octyl-9H-dibenzo[b,d]pyrrole-3-carbonitrile in 100 mL of THF was slowly added at −60° C. The new mixture was stirred for 30 minutes at −60° C., 3 hours at room temperature, then poured into 2N-HCl and extracted with ethyl acetate. The crude material obtained (25.4 g) was chromatographed on a silica gel column Hexane-ethyl acetate 4:1 eluted 11.2 g (71%) of 5-[(1,2,3,4-tetahydro-9-octyl-9H-dibenzo[b,d]pyrrol-6-yl)carbonyl]-2-furancarboxaldehyde as an orange oil.

EXAMPLE 156

Preparation of 5-[(1,2,3,4-tetrahydro-9-octyl-9H-dibenzo[b,d]pyrrol-6-yl)carbonyl]-2-furancarboxylic acid methyl ester To a mixture of 3.7 g of the aldehyde derivative from Example 155, 2.0 g of sodium cyanide and 10 g of activated manganese dioxide in 200 mL of methanol was added 1.0 g of acetic acid at room temperature. The reaction mixture was stirred for 2 hours at room temperature, filtered on celite and extracted with ethyl acetate. The crude material (3.5 g) was purified on a short pad of silica gel giving 2.9 g (73%) of 5-[(1,2,3,4-tetrahydro-9-octyl-9H-dibenzo[b,d]pyrrol-6-yl)carbonyl]-2-furancarboxylic acid methyl ester as a yellow oil.

EXAMPLE 157

Preparation of 5-[(1,2,3,4-tetrahydro-9-octyl-9H-dibenzo[b,d]pyrrol-6-yl)carbonyl]-2-furancarboxylic acid.

The hydrolysis of 2.9 g of methyl ester from Example 156 was carried out by using the conditions described in Example 137 except that a saturated solution of oxalic acid was used for the acidification of the reaction mixture instead of 2N-HCl. There was obtained 5-[(1,2,3,4-tetrahydro-9-octyl-9H-dibenzo[b,d]pyrrol-6-yl)carbonyl]-2-furan carboxylic acid (1.4 g; 50%) after repeated crystallizations from ethyl acetate as a yellow solid, mp 140.5°–42.5° C.

Anal. calcd for $C_{26}H_{31}NO_4$: C, 74.08; H, 7.41; N, 3.32. Found: C, 73.96; H, 7.37; N, 3.21.

EXAMPLE 158

Preparation of [5-(dimethoxymethyl)-2-furanyl]-(1,2,3,4-tetrahydro-9-octyl-9H-dibenzo[b,d]-pyrrol-6-yl)methanone A mixture of 11.2 g of aldehyde from Example 155, and 1.0 g of p-toluenesulfonic acid in 150 mL of methanol was refluxed for 2 hours. After evaporation of the solvent the residue was poured into a saturated solution of sodium bicarbonate and extracted with ethyl acetate. The material obtained as an orange-brown oil (11.9 g; 95%) was used without further purification.

EXAMPLE 159

Preparation of 5-[(1,2,3,4-tetrahydro-9-octyl-9H-dibenzo[b,d]pyrrol-6-yl) methyl]-2-furancarboxaldehyde A mixture of 2.9 g of furancarboxaldehyde dimethyl acetal from Example 164, 3.6 g of potassium carbonate, 2 mL of hydrazine in 50 mL of triethyleneglycol was heated at 180° C. for 2 hours. The reaction mixture was cooled and extracted with ethyl acetate, washed with water, dried over anhydrous magnesium sulfate to give 9.2 g of crude brown oil. This material was dissolved in 50 mL of THF and treated with 5 mL of 2N-HCl. After 1 hour of stirring at room temperature the reaction mixture was extracted with ethyl acetate, washed with brine and dried over anhydrous magnesium sulfate. Purification of the crude material on a silica gel column gave 1.4 g (55.7%) of 5-[(1,2,3,4-tetrahydro-9-octyl-9 H-dibenzo[b,d]pyrrol-6-yl)methyl ]-2-furancarboxaldehyde as an orange oil.

EXAMPLE 160

Preparation of 5-[(1,2,3,4-tetrahydro-9-octyl-9H-dibenzo[b,d]pyrrol-6-yl) methyl]-2-furancarboxylic acid To freshly prepared silver oxide obtained by treating 1.9 g of silver nitrate with 0.9 g of sodium hydroxide in 8 mL of water was added at 0°–5° C. a solution of 1.4 g of aldehyde from Example 159. After 2 hours of stirring at room temperature the reaction mixture was filtered on celite. The filtrate was acidified with 2N-HCl and the product extracted with ethyl acetate. Repeated crystallizations of the crude material (1.3 g) from ethyl acetate-hexane gave 0.8 g (54.7%) of 5-[(1,2,3,4-tetrahydro-9-octyl-9H-dibenzo[b,d]pyrrol-6-yl)-methyl]-2-furancarboxylic acid as a pale yellow solid, mp 152.5°–155.0° C.

Anal. calcd for $C_{26}H_{33}NO_3$: C, 76.62; H, 8.16; N, 3,44. Found: C, 76.48; H, 8.03; N, 3.39.

EXAMPLE 161

| Tablet Formulation (Wet Granulation) | | | | | |
|---|---|---|---|---|---|
| Item | Ingredients | mg/Tablet | | | |
| 1 | 5-[[1,2,3,4-tetrahydro-9-(4-chlorophenyl)methyl-9H-dibenzo[b,d]pyrrol-6-yl]-oxy]-2-furancarboxylic acid | 5 | 25 | 100 | 250 | 500 |
| 2 | Anhydrous Lactose | 103 | 83 | 35 | 19 | 24 |
| 3 | Povidone K30 | 5 | 5 | 6 | 12 | 24 |
| 4 | Croscarmellose Sodium | 6 | 6 | 8 | 161 | 32 |
| 5 | Magnesium Stearate | 1 | 1 | 1 | 3 | 6 |
| | Total Weight | 120 | 120 | 150 | 300 | 600 |

Manufacturing Procedure:
1. Mix Items 1, 2 and 3 in a suitable mixer for 15 minutes.
2. Granulate the powder mix from Step 1 with 20% PVP K30 Solution.
3. Dry the granulation from Step 2 at 50° C.
4. Pass the granulation from Step 3 through a suitable milling equipment.
5. Add the Item 4 to the milled granulation from Step 4 and mix for 3 minutes.
6. Compress the granulation from Step 5 on a suitable press.

EXAMPLE 162

| Capsule Formulation | | | | | |
|---|---|---|---|---|---|
| Item | Ingredients | mg/Capsule | | | |
| 1 | 5-[[1,2,3,4-tetrahydro-9-(4-chlorophenyl)methyl-9H-dibenzo[b,d]pyrrol-6-yl]-oxy]-2-furancarboxylic acid | 5 | 25 | 100 | 250 | 500 |
| 2 | Hydrous Lactose | 159 | 123 | 144 | — | — |
| 3 | Corn Starch | 25 | 35 | 401 | 35 | 70 |
| 4 | Talc | 10 | 15 | 10 | 121 | 24 |
| 5 | Magnesium Stearate | 1 | 2 | 2 | 3 | 6 |
| | Total Weight | 200 | 20 | 300 | 300 | 600 |

Manufacturing Procedure:
1. Mix Items 1, 2 and 3 in a suitable mixer for 30 minutes.
2. Add Items 4 and 5 and mix for 3 minutes.
3. Fill into a suitable capsule.

We claim:
1. A compound of the formula

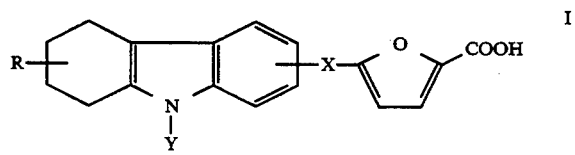

wherein R is hydrogen, alkyl$_{1-8}$, geminal alkyl$_{1-3}$, unsubstituted or substituted aryl; X is alkylene, —CR$_1$═CR$_2$— (E and/or Z), carbonyl, oxygen or sulfur, wherein one of R$_1$ and R$_2$ is alkyl$_{1-3}$ and the other is hydrogen; Y is unsubstituted alkyl$_{1-12}$ or substituted by one or more alkyl$_{1-3}$ groups, or unsubstituted or substituted phenylalkyl $_{1-3}$; or a salt thereof with a pharmaceutically acceptable base.

2. A compound in accordance with claim 1, wherein X is O or alkylene, Y is alkyl $_{4-9}$, phenylalkyl$_{1-3}$, and R is hydrogen geminal dimethyl, n-octyl or phenyl.

3. A compound in accordance with claim 1, wherein X is O, carbonyl or alkylene, R is hydrogen or geminal dialkyl and Y is n-octyl.

4. A compound in accordance with claim 1, wherein X is O, —CH=CH—(Z) or straight chain alkylene, R is hydrogen and Y is n-octyl.

5. A compound in accordance with claim 1, 5-[[1,2,3,4-tetrahydro-9-(4-chlorophenyl)methyl-9H-dibenzo[b,d]pyrrol-6-yl]oxy]-2-furancarboxylic acid.

6. A compound in accordance with claim 1, 5-[(1,2,3,4-Tetrahydro-9-octyl-9H-dibenzo[b,d]pyrrol-7-yl)oxy]-2-furancarboxylic acid.

7. A compound in accordance with claim 1, 5-[(1,2,3,4-Tetrahydro-9-octyl-9H-dibenzo[b,d]pyrrol-6-yl)carbonyl]-2-furancarboxylic acid.

8. A compound in accordance with claim 1, 5-[(1,2,3,4- Tetrahydro-9-octyl-9H-dibenzo[b,d]pyrrol-6-yl)methyl]-2furancarboxylic acid.

9. A compound in accordance with claim 1, (E)-5-[2(1,2,3,4-Tetrahydro-1,1-dimethyl-9-octyl-9H-dibenzo[b,d]pyrrol-6-yl)-ethenyl]-2-furancarboxylic acid.

10. A compound in accordance with claim 1, (E)-5-[2-Methyl-2-(1,2,3,4-tetrahydro-1,1-dimethyl-9-octyl-9H-dibenzo[b,d]-pyrrol-6-yl)ethenyl]-2-furancarboxylic acid.

11. A compound in accordance with claim 1, (Z)-5-[2-(1,2,3,4-Tetrahydro-9-octyl-9H-dibenzo[b,d]pyrrol-6-yl)ethenyl]-2-furancarboxylic acid.

12. A compound in accordance with claim 1, 5-[2-(1,2,3,4-Tetrahydro-9-octyl-9H-dibenzo[b,d]pyrrol-6-yl)ethyl]-2-furancarboxylic acid.

13. A compound in accordance with claim 1, 5-[(1,2,3,4-Tetrahydro-9-octyl-9H-dibenzo[b,d]pyrrol-6-yl )oxy]-2-furancarboxylic acid.

14. A pharmaceutical composition comprising a compound of the formula

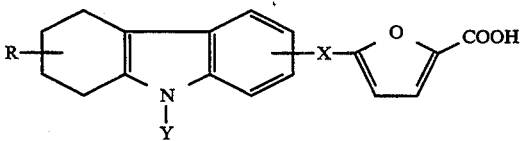

wherein R is hydrogen, alkyl$_{1-8}$, geminal alkyl$_{1-3}$, unsubstituted or substituted aryl; X is alkylene, —CR$_1$=CR$_2$— (E and/or Z), carbonyl, oxygen or sulfur, wherein one of R$_1$ and R$_2$ is alkyl$_{1-3}$, and the other is hydrogen; Y is unsubstituted alkyl$_{1-12}$ or substituted by one or more alkyl$_{1-3}$ groups, or unsubstituted or substituted phenylalkyl $_{1-3}$; or a salt thereof with a pharmaceutically acceptable base, and an inert carrier.

15. A pharmaceutical composition in accordance with claim 14, wherein X is O or alkylene, Y is alkyl$_{4-9}$, phenylalkyl$_{1-3}$, and R is hydrogen geminal dimethyl, n-octyl or phenyl.

16. A pharmaceutical composition in accordance with claim 14, wherein X is O, carbonyl or alkylene, R is hydrogen or geminal dialkyl and Y is n-octyl.

17. A pharmaceutical composition in accordance with claim 14, wherein X is O, —CH=CH—(Z) or straight chain alkylene, R is hydrogen and Y is n-octyl.

18. A pharmaceutical composition in accordance with claim 14, wherein the compound of formula I is, 5-[[1,2,3,4-tetrahydro-9-(4-chlorophenyl)methyl-9H-dibenzo[b,d]pyrrol-6-yl]-oxy]-2-furancarboxylic acid.

19. A pharmaceutical composition in accordance with claim 14, wherein the compound of formula I is, 5-[(1,2,3,4-Tetrahydro-9-octyl-9H-dibenzo[b,d]pyrrol-7-yl)oxy]-2-furancarboxylic acid.

20. A pharmaceutical composition in accordance with claim 14, wherein the compound of formula I is, 5-[(1,2,3,4-Tetrahydro-9-octyl-9H-dibenzo[b,d]pyrrol-6-yl)carbonyl]-2-furancarboxylic acid.

21. A pharmaceutical composition in accordance with claim 14, wherein the compound of formula I is, 5-[(1,2,3,4-Tetrahydro-9-octyl-9H-dibenzo[b,d]pyrrol-6-yl)methyl]-2-furancarboxylic acid.

22. A method inhibiting phospholipase A$_2$, in a host requiring such treatment, which comprising administering an effective amount of a compound of the formula

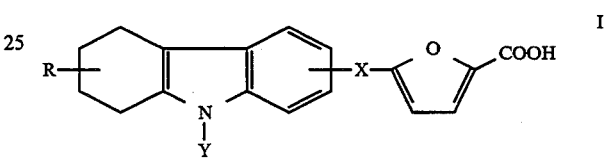

wherein R is hydrogen, alkyl$_{1-8}$, geminal alkyl$_{1-3}$, unsubstituted or substituted aryl; X is alkylene, —CR$_1$=CR$_2$— (E and/or Z), carbonyl, oxygen or sulfur, wherein one of R$_1$ and R$_2$ is alkyl$_{1-3}$, and the other is hydrogen; Y is unsubstituted alkyl$_{1-12}$ or substituted by one or more alkyl$_{1-3}$ groups, or unsubstituted or substituted phenylalkyl $_{1-3}$; or a salt thereof with a pharmaceutically acceptable base.

23. A method in accordance with claim 22, wherein X is O or alkylene, Y is alkyl $_{4-9}$, phenylalkyl, and R is hydrogen geminal dimethyl, n-octyl or phenyl.

24. A method in accordance with claim 22, wherein X is O, carbonyl or alkylene, R is hydrogen or geminal dialkyl and Y is n-octyl.

25. A method in accordance with claim 22, wherein X is O, —CH=CH—(Z) or straight chain alkylene, R is hydrogen and Y is n-octyl.

26. A method in accordance with claim 22, wherein the compound of formula I is, 5-[[1,2,3,4-tetrahydro-9-(4-chlorophenyl)methyl-9H-dibenzo[b,d]pyrrol-6-yl]-oxy]-2-furancarboxylic acid.

27. A method in accordance with claim 22, wherein the compound of formula I is, 5-[(1,2,3,4-Tetrahydro-9-octyl-9H-dibenzo[b,d]pyrrol-7-yl)oxy]-2-furancarboxylic acid.

28. A method in accordance with claim 22, wherein the compound of formula I is, 5-[(1,2,3,4-Tetrahydro-9-octyl-9H-dibenzo[b,d]pyrrol-6-yl)carbonyl]-2-furancarboxylic acid.

29. A method in accordance with claim 22, wherein the compound of formula I is, 5-[(1,2,3,4-Tetrahydro-9-octyl-9H-dibenzo[b,d]pyrrol-6-yl)methyl]-2-furancarboxylic acid.

* * * * *

UNITED STATES PATENT AND TRADEMARK OFFICE
CERTIFICATE OF CORRECTION

PATENT NO. : 5,451,600

DATED : September 19, 1995

INVENTOR(S) : Bruce Lester Banner, Giuseppe Federico Weber

It is certified that error appears in the above-indentified patent and that said Letters Patent is hereby corrected as shown below:

On the title page, item [54] and in column 1, lines 2-5, in the title "SUBSTITUTED TETRAHYDROBENZOPYRROLYLFURANOIC ACID DERIVATIVES AS PHOSPHOLIPASE $A_2$ INHIBITORS", which is incorrect, the title should read --SUBSTITUTED TETRAHYDRODIBENZOPYRROLYLFURANOIC ACID DERIVATIVES AS PHOSPHOLIPASE $A_2$ INHIBITORS-- .

UNITED STATES PATENT AND TRADEMARK OFFICE
CERTIFICATE OF CORRECTION

PATENT NO. : 5,451,600
DATED : September 19, 1995
INVENTOR(S) : Bruce Lester Banner, Giuseppe Federico Weber It is certified that error appears in the above-indentified patent and that said Letters Patent is hereby corrected as shown below:

IN THE CLAIMS:

- Claim 8, Column 55, lines 22-23: "5-[(1,2,3,4-Tetrahydro-9-octyl-9H-dibenzo[b,d]pyrrol-6-yl)methyl]-2furancarboxylic acid" should read -- 5-[(1,2,3,4-Tetrahydro-9-octyl-9H-dibenzo[b,d]pyrrol-6-yl)methyl]-2-furancarboxylic acid. -- .

Signed and Sealed this

Fifth Day of December, 1995

Attest:

BRUCE LEHMAN

Attesting Officer

Commissioner of Patents and Trademarks